United States Patent
Manhas et al.

(10) Patent No.: US 9,999,218 B2
(45) Date of Patent: *Jun. 19, 2018

(54) PEST CONTROL FORMULATIONS AND METHODS OF MAKING AND USING SAME

(71) Applicant: 0903608 B.C. Ltd., Vancouver (CA)

(72) Inventors: Karan Manhas, Vancouver (CA); Annett Rozek, Port Moody (CA)

(73) Assignee: 0903608 B.C. LTD., Vancouver, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/248,189

(22) Filed: Apr. 8, 2014

(65) Prior Publication Data

US 2014/0220164 A1    Aug. 7, 2014

Related U.S. Application Data

(63) Continuation-in-part of application No. 14/347,219, filed as application No. PCT/IB2012/055348 on Oct. 4, 2012.

(60) Provisional application No. 61/652,110, filed on May 25, 2012, provisional application No. 61/622,893, filed on Apr. 11, 2012, provisional application No. 61/542,993, filed on Oct. 4, 2011.

(51) Int. Cl.

| A61K 36/00 | (2006.01) |
|---|---|
| A01N 25/02 | (2006.01) |
| A01N 35/04 | (2006.01) |
| A01N 37/36 | (2006.01) |
| A01N 31/02 | (2006.01) |

(52) U.S. Cl.
CPC ............. *A01N 25/02* (2013.01); *A01N 31/02* (2013.01); *A01N 35/04* (2013.01); *A01N 37/36* (2013.01)

(58) Field of Classification Search
CPC ....................................................... A61K 36/00
USPC ......................................................... 424/725
See application file for complete search history.

(56) References Cited

U.S. PATENT DOCUMENTS

| 2,793,154 | A | 5/1957 | Shillitoe |
| 2,897,112 | A | 7/1959 | Harford |
| 4,283,878 | A | 8/1981 | Hill |
| 4,556,562 | A | 12/1985 | Larson |
| 4,943,434 | A | 7/1990 | Lidert |
| 5,001,146 | A | 3/1991 | Carter |
| 5,145,604 | A | 9/1992 | Neumiller |
| 5,405,612 | A | 4/1995 | Locke |
| 5,472,700 | A | 12/1995 | Staetz |
| 5,679,662 | A | 10/1997 | Chang |
| 5,738,863 | A | 4/1998 | Sackin et al. |
| 5,792,465 | A | 8/1998 | Hagarty |
| 5,885,600 | A | 3/1999 | Blum |
| 5,900,244 | A | 5/1999 | Howse |
| 6,294,571 | B1 | 9/2001 | Subbaraman |
| 6,641,827 | B2 | 11/2003 | Yoshida |
| 6,703,034 | B2 | 3/2004 | Parmar |
| 6,707,616 | B1 | 3/2004 | Takahashi et al. |
| 6,949,587 | B1 * | 9/2005 | Bessette ................. A01N 31/04 514/730 |
| 7,381,431 | B2 | 6/2008 | Baker |
| 7,687,533 | B2 | 3/2010 | Critcher |
| 7,955,609 | B2 | 6/2011 | Baron |
| 8,105,620 | B2 * | 1/2012 | Williams ............... A01N 65/00 424/405 |
| 8,119,150 | B2 | 2/2012 | Tamarkin |
| 2008/0269177 | A1 | 10/2008 | Bessette |
| 2009/0257958 | A1 * | 10/2009 | Sims ...................... A01N 27/00 424/45 |
| 2010/0120724 | A1 | 5/2010 | Bessette |
| 2011/0070308 | A1 | 3/2011 | Williams et al. |
| 2011/0229589 | A1 | 9/2011 | Elraz |
| 2014/0208636 | A1 | 7/2014 | Black |
| 2014/0242199 | A1 | 8/2014 | Manhas |

FOREIGN PATENT DOCUMENTS

| CA | 2068039 | A1 | 6/1983 |
| CN | 1276161 | A | 12/2000 |
| CN | 1513319 | A | 7/2004 |
| CN | 1633849 | A | 7/2005 |
| CN | 101296710 | A | 10/2008 |
| CN | 101442908 | A | 5/2009 |
| CN | 101448394 | A | 6/2009 |
| CN | 101537044 | A | 9/2009 |
| CN | 102091337 | A | 6/2011 |
| CN | 102171321 | A | 8/2011 |
| CN | 1322110 | A | 11/2011 |
| EP | 0494067 |  * | 7/1992 |
| EP | 0948892 | A1 | 10/1999 |
| EP | 2250904 | A1 | 11/2010 |
| GB | 2405340 |  | 3/2005 |
| JP | S50-42053 |  | 4/1975 |

(Continued)

OTHER PUBLICATIONS

Gahukar, R.T., "Formulations of neem-based products/pesticides", Pestology, 1996, XX(9):44-55.
English Translation of Office Action dated Mar. 13, 2015 issued for related Chinese patent application No. 201280059656.X, 9 pages.
Extended European Search Report dated Mar. 30, 2015 issued for related European patent application No. 12839114.1, 7 pages.
Abbassy, M.A., et al., "Insecticidal and synergistic effects of Majorana hortensis essential oil and some of its major constituents", Entomologia Experimentalis et Applicata, 2009, 131(3):225-232.
Ahmed, K.S., et al., "Effects of plant oils on oviposition preference and larval survivorship of Callosobruchus chinesis on azuki bean", Applied Entomology and Zoology, 1999, 34(4):547-550.
Ansari, M.A., et al. "Larvicidal and mosquito repellent action of peppermint (*Mentha piperita*) oil", Bioresource Technology, 2000, 71(3):267-271.

(Continued)

*Primary Examiner* — Michael V Meller
(74) *Attorney, Agent, or Firm* — Oyens Wiggs Green & Mutala LLP

(57) ABSTRACT

Compositions useful for controlling pests are disclosed. In some embodiments, the composition includes a pesticidal natural oil and a polar aromatic solvent or an alkyl alcohol solvent. Methods of making and using the compositions are disclosed.

22 Claims, 3 Drawing Sheets

(56) References Cited

FOREIGN PATENT DOCUMENTS

| | | |
|---|---|---|
| JP | 6396101 A | 4/1988 |
| JP | 36438006 | 2/1989 |
| JP | H04308511 | 10/1992 |
| JP | H05139907 A | 6/1993 |
| JP | 610122 B2 | 2/1994 |
| JP | H08267086 | 10/1996 |
| JP | 2000247809 A | 9/2000 |
| JP | 2000281509 A | 10/2000 |
| JP | 2001199807 A | 7/2001 |
| JP | 2002-511391 A | 4/2002 |
| JP | 2002521406 | 7/2002 |
| JP | 200312411 A | 1/2003 |
| JP | 2005513053 A2 | 5/2005 |
| JP | 2005255664 | 9/2005 |
| JP | 2006306835 * | 11/2006 |
| JP | 2010515775 A | 5/2010 |
| JP | 2010522236 A | 7/2010 |
| JP | 2011517685 | 6/2011 |
| WO | 30/05964 | 2/2000 |
| WO | 01/00034 A1 | 1/2001 |
| WO | 2009/144712 A2 | 12/2009 |
| WO | 2012107266 A1 | 8/2012 |
| WO | 20131050967 A1 | 4/2013 |

OTHER PUBLICATIONS

Arslan, N., et al., "Variation in essential oil content and composition in Turkish anise (*Pimpinella anisum* L.) populations", Turk. J. Agri. For., 2004, 28:173-177.

Avato, P., et al., "Allysulfide constituents of garlic volatile oil as antimicrobial agents", Phytomedicine, 2000, 7 (3):239-243.

Barnard, D.R., "Repellency of essential oils to mosquitoes (*Diptera culicidae*)", Journal of Medical Entomology, 1999, 36(5):625-629.

Brahmachari, G. "Neem—an omnipotent plant: a retrospection", Chembiochem, 2004, 5:408-421.

Chaieb, K., et al., "The chemical composition and biological activity of clove essential oil, Eugenia caryophyllata (*Syzigium aromaticum* L. Myrtaceae): a short review", Phytotherapy Research, 2007, 21(6):501-506.

Chang, K.S. and Ahn, Y.T., "Fumigant activity of (E)-anethole identified in Illicium verum fruit against Blatella germanica", Pest Manage. Sci., 2001, 58:161-166.

Chang, S.T. and Cheng, S.S., "Antitermitic activity of leaf essential oils and components from Cinnamomum osmophleum", J. Agric. Food Chem., 2002, 50:1389-1392.

Chastrette, M., et al., "Approach to general classification of solvents using a multivariate statistical treatment of quantitative solvent parameters", Journal of the American Chemical Society, 1985, 107(1):1520-1526.

Cheng, S.S., et al., "Variations in insecticidal activity and chemical compositions of leaf essential oils from Cryptomeria japonica at different ages", Bioresource Tech., 2009, 100(1):465-470.

Choi, W., et al., Toxicity of plant essential oils to Tetranychus urticae (Acari:Tetranychidae) and Phytoseiulus persimilis (Acari:Phytoseiidae), Journal of Economic Entomology, 2004, 97(2):553-558.

Clark, R.J. and Menary, R.C., Variations in compositions of peppermint oil in relation to production areae, Econ. Bot., 1981, 35:59-69.

Daniel, S.H. and Smith, R.H., "The repellent effect of neem (*Azadirachta indica* A Juss) oil and its residual efficacy against Callosobruchus maculatus on cowpea", in Fleurat-Lessard, F, & Ducom, P. eds (Proceedings Fifth International Working Conference on Stored-Product Protection) (Bordeaux, 1990), 1589-1597.

Don-Pedro, K.M., "Investigation of single and joint fumigant insecticidal action of citrus peel oil components", Pestic. Sci., 1996, 46:79-84.

Ellis, M.D., and Baxendale, F.P., "Toxicity of seven monoterpenoids to tracheal mites (Acari: Tarsonemidae) and their honey bee (Hymenoptera: Apidae) hosts when applied as fumigants", J. Econ. Entomol, 1997, 90:1087-1091.

Erbilgin, et al., Acetophenone as an anti-attractant for the Western Pine Beetle, *Dendroctonus brevicomis* Leconte, J Chem Ecol, 2007, 33:817-823.

Franzios, G., et al., "Insecticidal and genotoxic activities of mint essential oils", J. Agric. Food Chem., 1997, 45:2690-2694.

Fuhremann, T.W., et al,. "Effects of naturally occurring food plant components on insecticide degradation in rats", J. Agri. Food Chem., 1978, 26(5):1068-1075.

Gochev, V., et al., "Chemical composition and antimicrobial activity of Bulgarian peppermint oils", Bulgaria Scientific Papers, 2008, 36(5):83.

Granger & Passet, "Thymus vulgaris spontane de France: Races chimiques et chemotaxonomie", Phytochemistry, 1973, 12(7):1683-1691.

Harwood, S.H., et al., "Toxicity of peppermint monoterpenes to the variegated cutworm (Leptidoptera: Noctuidae)", J. Econ. Entomol, 1990, 83:1761-1767.

Hierro, I., et al., "Action of different monoterpenic compounds against Anisakis simplex S.I.L. larvae", Phytomedicine 2004, 11:77-82. '.

Hui, L., et al., "Chemical composition of lavender essential oil and its antioxidant activity and inhibition against rhinitisrelated bacteria", Afri. J. of Micro. Res., 2010, 4(4):309-313.

Hummelbrunner, a.L., et al., "Acute, sublethal, antifeedant and synergistic effects of monoterpenoid essential oil compounds on the tobacco cut worm (Lepidoptera: Noctuidae)", J. Agric. Food Chem., 2001, 49:715-720.

Isman, M.B., et al., "Pesticides based on plant essential oils: from traditional practice to commercialization", Naturally Occurring Bioactive Compounds, 2006, 3(2):29-44.

Jones, C. And Firn, R., "Some allelochemicals of Ptteridium aquilinum and their involvement in resistance to Pieris brassicae", Biochem. Syst. Ecol, 1979, 7:187-192.

Karr, L.L. And Coats, J.R., "Effects of four monoterpenoids on growth and reproduction of the German cockroach (Blattodea: Blattellidae)", J. Econ. Entomol, 1992, 85:424-429.

Kaul, P.N., et al., Volatile constituents of essential oils isolated from different parts of cinnamon (*Cinnamomum zeylanicum* Blume), J. Sci. Food Agri., 2003, 83:53-55.

Khattak, M.K., et al., "Repellency and residual effect of neem or mineral oil on the distribution and oviposition of maize weevil, *Sitophilus zeamais* Motsch", Pakistan Journal of Biological Sciences, 2000, 3(12): 2131-2134.

Kim, E.H., et al., "Acaricidal activity of clove bud oil compounds against Dermatophagoides farinae and Dermatophagoides pteronyssinus (Acari: Pyroglyphidae)", J. Agric Food Chem, 2003, 51:885-889.

Kimbaris, A.C., et al., "Quantitative analysis of garlic (*Allium sativum*) oil unsaturated acyclic components using FTRaman spectroscopy", Food Chemistry, 2006, 94(2):287-295.

Lee, S., et al., "Insecticidal activity of monoterpenoids to western corn root worm (Coleoptera: Chrysomelidae), spotted spidermite (Acari: Tetranychidae) and Housefly (Diptera: Muscidae)", J. Econ. Entomol, 1997, 90:883-892.

Lota, M.L., et al., "Volatile components of peel and leaf oils of lemon and lime species", J. Agri. Food Chem., 2002, 50:796-805.

Marcus C. and Lichtenstien, P., "Biologically active components of anise: toxicity and interactions with insecticides in insects", J. Agri. Food Chem., 1979, 27(6):1217-1223.

Miresmailli, S., et al., "Comparative toxicity of Rosmarinus officinalis L. essential oil blends of its major constituents against Tetranychus urticae Koch 20 (Acari: Tetranychidae) on two different host plants", Pest Manag Sci, 2006, 62:366-371.

Mishra, a.K., et al., "Use of neem oil as a mosquito repellent in tribal villages of mandla district, madhya pradesh", Indian J Malariol, 1995, 32(3):99-103.

Momen, F.M., et al., "Influence of mint and peppermint on Tetrynychus urticae and some predacious mites of the Family Phytoseiidae (Acari: Tetranychidae: Phytoseiidae)", Acta Phytopathologica et Entomologica Hungaria, 2001, 36 (1-2):143-153.

(56) References Cited

OTHER PUBLICATIONS

Naqvi, S.N.H., et al., "Comparative toxicity of RB-A [Neem Formulation] and Malathion against bed bugs", Proceedings of Pakistan Congress of Zoology, 1993, 13:369-377.

National Research Council, Board on Science and Technology for International Development, Ad Hoc Panel Report,. Neem: A Tree for Solving Global Problems, Washington: National Academy Press, 1992.

Obeng-Ofori, D., et al., "Bioactivity of eugenol, a major component of essential oil of Ocimum suvae (wild) against four species of stored product coleopteran", Int. J. Pest Manag. 1997, 43:89-94.

Pavela, R., et al., "Effectiveness of Neem (azidirachta indica) insecticides against Brassica pod midge (Dasinera brassicae Winn.)", Journal of Pest Science, 2009, 82(3):235-240.

Perrucci, S., et al., "Therapeutic efficacy of linalool for the topical treatment of parasitic otitis caused by Psoroptes cuniculi in the rabbit and in the goat", Med. Vet. Entomol, 1997, 11:300-302.

Rahman, A and Talukder, F.A., "Bioethcacy of some plant derivatives that protect grain against the pulse beetle, *Callosobruchus maculatus*", Journal of Insect Science, 2006, 6:03.

Rajeswara, Rao, B.R., et al., "Volatile flower oils of three genotypes of rose-scented geranium (*Pelargonium* sp.)", Flavour Frag J. , 2000, 15:105-107.

Romero, A., et al., Insecticide resistance in the bed bug: a factor in the pest's sudden resurgence, J Med Entomol, 2007, 44(2):175-178.

Salom, S.M., et al., "Laboratory evaluation of biologically-based compounds as antifeedants for the pales weevil, hulobius-pale (Herbst)", J. Entomol, Sci., 1994, 29:407-419.

Samarasekera, R., "Mosquitocidal activity of leaf and bark essential oils of Ceylon Cinnamomum zeylanicum", Journal of Essential Oil Research, 2005, 17(3):301-303.

Santos, P.M., et al., "Essential oils from hairy root cultures and fruits and roots of Pimpinella anisum", Phytochemistry, 1998, 48:455-460.

Schmahl, G., et al., "The efficacy of neem seed extracts (Tre-San, MiteStop) on broad spectrum of pests and parasites", Parasitology Research, 2010, 107(2):261-269.

Schmutterer, "Properties and potential of natural pesticides from the neem tree, *Azadirachta indica*", Annu Rev Entomol, 1990, 35:271-297.

Shabnum, S. and Wagay, M., "Essential oil composition of Thymus vulgaris L. and their uses", Journal of Research & Development, 2011, 25(11):83-94.

Shellie, R., et al., "Characterisation of lavender essential oils by using gas chromatography-mass spectrometry with correlation of linear retention indices and comparison with comprehensive two-dimensional gas chromatography", J. Chromatog. A., 2002, 970:225-234.

Simic, A., et al., "The chemical composition of some Lauraceae essential oils and their antifungal activities", Phytother. Res. 2004, 18:713-717.

Thompson, J., et al., "Qualitative and quantitative variation in monoterpene co-occurrence and composition in the essential oil of Thymus vulgaris chemotypes", J. Chem Ecol, 2003, 29:859.

Toncer, O., et al., "Changes in essential oil composition of oregano (*Origanum onites* L.) due to diurnal variations at different development stages", Notulae Botanicae Horti Agrobotanici Cluj, 2009, 37(2):177-181.

Traboulsi, A.F., et al., "Insecticidal properties of essential plant oils against the mosquito *Culex pipiens molestus* (Diptera: Culicidae)", Pest Manag Sci, 2002, 58(5):491-495.

Tripathi, A.K., et al., "Effects of volatile oil constituents of *Mentha* species against stored grain pests, Callosobruchus maculatus and Tribolium castanum", J. Med Arom Plant Sci, 2000, 22:549-556.

Tripathi, A.K., et al., "Toxicity, feeding deterrence, and effect of activity of 1, 8-cineole from Artemisia annua on progeny production of Tribolium castanaeum (Coleoptera: Tenebrionidae)", J. Econ. Entomol, 2001, 94:979-983.

Trongtokit Y., et al., "Comparative repellency of 38 essential oils against mosquito bites", Phytotherapy Res, 2005, 19:303-309.

Vasudeva, N. and Sharma, T., "Chemical composition and antimicrobial activity of essential oil of citrus limettioides Tanaka", Journal of Pharmaceutical Technology and Drug Research, 2012, 1(1):2.

Vokou, D., et al., "Geographic variation of Greek oregano (*Origanum vulgare* ssp. *hirtum*) essential oils", Biochem Syst Ecol, 1993, 21:287-295.

Webb, et al, On the penetration of insecticides through the insect cuticle (Cooper Technical Bureau: Berkhamsted) , Journal of Experimental Biology, 1945, 22:8-20.

Xia, Y., et al., The molecular and cellular bassis of olfactory-driven behaviour in Anopheles gambiae larvae, Proceedings of the National Academy of Sciences of the USA, 2008, 105:6433-6438.

Yang, Y.C. et al., "Ovicidal and adulticidal effects of Eugenia caryophyllata bud and leaf oil compound on Pediculus capitis", J Agri Food Chem, 2003, 51:4884-4888.

Yang, Y.C., et al., Ovicidal and adulticidal activities of Cinnamomum zeylanicum bark essential oil compounds and related compounds against Pediculus humanus capitis (Anoplura: Pediculidae), Int J Parasitol, 2005, 35:1595-1600.

Product labels for CIRKIL CX and CIRKIL RTU products, first sold in the United States on or about Jun. 25, 2012.

\* cited by examiner

PEST CONTROL FORMULATIONS AND METHODS OF MAKING AND USING SAME

REFERENCE TO RELATED APPLICATIONS

This application is a continuation-in-part of U.S. patent application Ser. No. 14/347,219 filed 4 Oct. 2012, which is a 371 of Patent Cooperation Treaty patent application No. PCT/IB2012/055348 filed 4 Oct. 2012, which claims the benefit of each of U.S. provisional patent application No. 61/542,993 filed 4 Oct. 2011, U.S. provisional patent application No. 61/622,893 filed 11 Apr. 2012, and U.S. provisional patent application No. 61/652,110 filed 25 May 2012. Each of the foregoing applications is hereby incorporated by reference herein in its entirety.

TECHNICAL FIELD

Some embodiments of the present invention pertain to compositions that can be used to control a variety of pests. Some embodiments of the present invention can be used to control arthropods, including insects and arachnids, and/or other pests. Some embodiments of the present invention can be used to control sucking and biting pests, including e.g. bed bugs, mosquitoes, ticks, lice, stink bugs, flies, cockroaches and moths. Some embodiments of the invention pertain to methods of using compositions to control pests. Other embodiments of the invention pertain to methods of making compositions to control pests.

BACKGROUND

Pest control is an ongoing, worldwide problem. In addition to physical means of control that have been practiced for centuries, recent decades have witnessed the emergence and widespread use of hundreds of chemically developed pest repellents, growth regulators, and insecticides. These products are frequently synthetic varieties that are heavily refined prior to commercialization—the list includes the pyrethroids (including deltamethrins, cyfluthryns, etc), DEET and other aromatic amides, organophosphates, and carbamates. The usefulness of these products is often limited by factors including human or environmental toxicity, insect resistance (particularly to pyrethroids; see e.g. Romero, et al.), limited dry residue activity, repellancy and physical factors that make them inappropriate for indoor use (odor, staining). For these reasons and due to shifting consumer preference paradigms, there is consistently increasing demand for naturally-derived, effective pest control products that overcome these limitations.

Some pesticide products are derived from botanical and other natural sources; for example the pyrethrin classes of pesticides are derived from the pyrethrum daisy, *Chrysanthemum cinerariaefolium*. Other examples include: rotenone, from the roots of *Derris Lonchocarpus*; *ryania*, from the stems of *Ryania speciosa*; and neem, derived from the leaves, bark, and seeds of *Azadirachta indica*.

The tree *Azadirachta indica*—in some cases referred to as the "Sacred Tree" or "Nature's Pharmacy"—has long been recognized as a source of a wide variety of useful bioactive compounds. Neem derivatives have demonstrated effectiveness as moisturizing agents, and neem oil itself has been used as a treatment for various skin conditions including acne, psoriasis, and chicken pox. It is also used in toothpastes, as a cooking ingredient, and in pharmaceuticals for treating a range of symptoms including fever, earache, headache, and serious disorders including diabetes (see e.g. Brachmachari). In the agricultural sector, neem oil is considered an effective measure for the prevention of mildew, anthracnose, rust, leaf spot, *botrytis*, scab and *alternaria*. Its derivatives have furthermore been described variously as antiviral, antimicrobial, antifungal, and antiseptic. Neem oil and many of its derivatives have also been recognized and used as insect control agents and pesticides.

Neem oil contains dozens of active compounds that kill or repel insects, with demonstrated efficacy against more than 375 insect species. It has been recognized as a repellent of many pests, particularly insects (see e.g. Mishra, et al). At higher concentrations it has been reported to demonstrate repellency activity against some insects for up to six months after application (see Daniel & Smith). These repellency characteristics limit neem oil's insecticidal activity significantly, since insects are repelled from exposure to the very product that is intended to be insecticidal. Neem oil has been shown to prevent egg emergence of some insects when eggs are treated directly with the oil: See Rahman & Talukder; Ahmed, et al. Neem oil also demonstrates some prevention of oviposition—of a limited subset of insects—at higher concentrations (including the maize weevil; see M K Khattak).

Current hypotheses suggest that neem oil may work as a contact killer, as an antifeedant, as an insect-growth regulator, a sterilizing agent, a gut motility inhibitor, and/or as a chitin inhibitor. Azadirachtin—an important active ingredient in neem oil—has been reported to exhibit antifeedant, repellent, and sterilization activities under certain circumstances and has been used as a pest control chemical in the past (see U.S. Pat. No. 4,556,562).

Neem oil and azadirachtin are believed to exhibit complex mechanisms of insect toxicity, including activity upon insect hormonal systems, antifeedant activity, anti-molting activity, and numerous other activities. Neem oil as a pesticide is biodegradable and of low environmental and human toxicity, exempted from the tolerance requirement by the United States EPA (see United States Federal Register, Volume 60, Number 239, 1995).

Neem oil has drawbacks as an insecticide. While effective at preventing molting and exhibiting certain repellency characteristics in some insects, reports of neem oil's knockdown capability are inconsistent (see e.g. Schumutter), and some studies find it less efficient at killing adult insects than related pesticides (see Pavela). Neem oil has been reported to have poor dry residue pesticidal activity against most insects, and poor dry residual prevention of egg emergence and prevention of oviposition against most species of insects. Neem oil has an odor that is offensive to some people, and its odor does not rapidly disperse.

Other natural oils have been reported to exhibit insecticidal or other pest control activities, as are described further below.

Pests are a considerable annoyance and health risk. For example, in recent years, there has been a resurgence of bed bug (*Cimex lectularius* L.) infestations across North America. Bed bugs cause sleeplessness, anxiety, and discomfort for those affected. Bed bugs are troublesome pests. They live and hide in crevices, seams and other small spaces. They are hard to identify and locate, and can survive dormant for months or a year or more without feeding. They spread by clinging to suitcases, furniture and clothing which people bring with them from place to place. Current methods of bed bug control are expensive and have various limitations, particularly because products must be applied in sleeping areas where the affected individuals are subject to close and lengthy exposure.

There remains a need for improved pesticides derived from natural sources, pesticides that can prevent egg eclosion, and pesticides having improved dry residue and prolonged residual activity.

SUMMARY

Some embodiments of the present invention provide pesticidal compositions containing a pesticidal natural oil and/or a component thereof and/or a derivative thereof and a polar aromatic solvent. Some embodiments can be used to control pests by killing the pests, preventing or reducing feeding, preventing or reducing oviposition, preventing or reducing eclosion of their eggs, or the like. Some embodiments exhibit effective or more rapid knockdown pesticidal activity, dry residue pesticidal activity and/or prolonged residual pesticidal activity. Some embodiments can be used to control pests including insects and/or arachnids, including arthropods such as bed bugs.

In some embodiments, the pesticidal natural oil is neem oil, clove oil, peppermint oil, mint oil, cinnamon oil, thyme oil, oregano oil, and/or garlic oil and/or derivatives or extracts thereof. In some embodiments, the polar aromatic solvent is selected from the group consisting of: aryl ketones, aryl alcohols, aryl-alkyl alcohols, aryl aldehydes, aryl-alkyl ketones, aryl-aryl ketones, aryl carboxylic acids, aryl esters, aryl-alkyl esters, aryl-aryl esters, aryl-alkyl ethers, and aryl-aryl ethers. In some embodiments, the polar aromatic solvent is an aryl ketone such as acetophenone. In some embodiments, the polar aromatic solvent is acetophenone, benzyl alcohol, ethyl benzoate and/or benzoic acid. In some embodiments, the pesticidal natural oil is neem oil and the polar aromatic solvent is acetophenone.

In some embodiments, the combination of the natural pesticidal oil and the polar aromatic solvent exhibits a synergistic level of pesticidal activity. In some embodiments, the combination of the pesticidal natural oil and the polar aromatic solvent is effective as a pesticide wherein each of the pesticidal natural oil and the polar aromatic solvent are present at a concentration below the concentration at which the pesticidal natural oil or the polar aromatic solvent would exhibit similar pesticidal activity if used alone. In some such embodiments, the polar aromatic solvent is acetophenone and the pesticidal natural oil is neem oil, clove oil, cinnamon oil, thyme oil, oregano oil and/or garlic oil.

DETAILED DESCRIPTION

Figure 1:
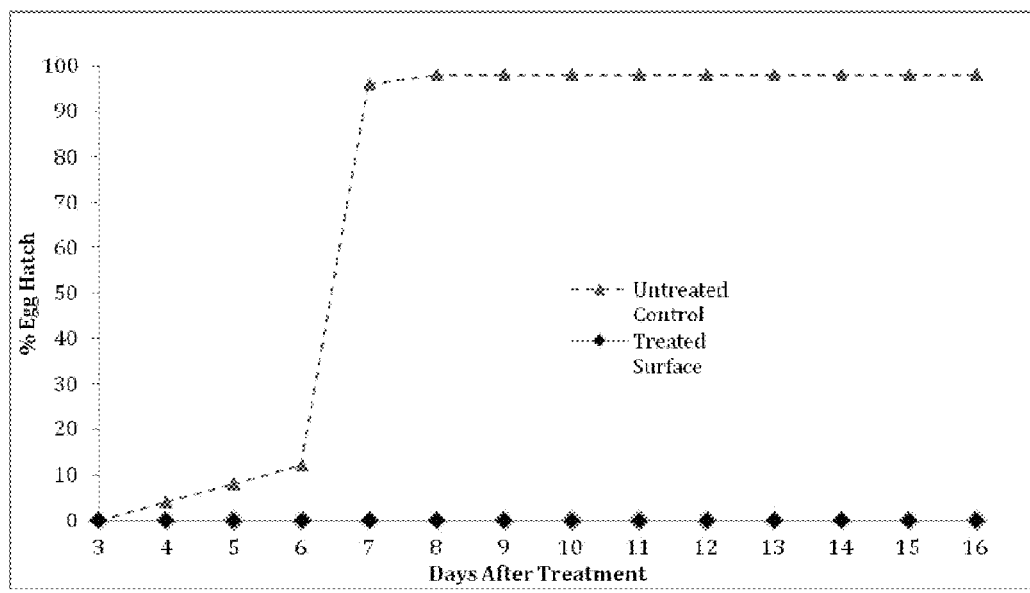
FIG. 1 shows the results of an example testing the prevention of egg emergence by a composition in accordance with one embodiment of the invention.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Where a range of values is provided, it is understood that each intervening value, to the tenth of the unit of the lower limit unless the context clearly dictates otherwise, between the upper and lower limit of that range and any other stated or intervening value within that stated range is encompassed within embodiments of the invention. The upper and lower limits of these smaller ranges may independently define a smaller range of values, and it is to be understood that these smaller ranges are intended to be encompassed within embodiments of the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present invention, preferred methods and materials are described to avoid unnecessarily obscuring the disclosure.

As used herein, "comprises" or "comprising" are to be interpreted in their open-ended sense, i.e. as specifying that the stated features, elements, steps or components referred to are present, but not excluding the presence or addition of further features, elements, steps or components.

As used herein, singular forms include plural references unless the context clearly dictates otherwise. For example, "a fungus" also encompasses "fungi".

As used herein, the term "pest" refers to organisms that negatively affect a host—such as a plant or an animal such as a mammal—by colonizing, damaging, attacking, competing with them for nutrients, or infecting them. This includes arthropods including insects and arachnids, and includes sucking and biting pests such as bed bugs, mites, ticks, ants, lice, and cockroaches.

As used herein, the term "pesticide" refers to an agent that can be used to control and/or kill a pest. The term is understood to encompass, but is not limited to, naturally occurring or synthetic chemical insecticides (larvicides, adulticides, ovicides), acaricides (miticides), fungicides, nematicides, parasiticides, or other control agents. "Pesticidal activity" refers to an agent that is active as a pesticide.

As used herein, the term "egg emergence" means eclosion; that is, the emergence of an adult insect from its pupal case or the hatching of an insect larva/nymph from an egg. "Preventing eclosion" or "preventing egg emergence" means preventing or delaying the emergence of an adult insect from its pupal case or the hatching of an insect larva from an egg.

As used herein, the terms "control" or "controlling" are meant to include, but are not limited to, any killing, growth regulating, or pestistatic (inhibiting or otherwise interfering with the normal life cycle of the pest) activities of a composition against a given pest. These terms include for example sterilizing activities which prevent the production of ova or sperm, including preventing vitellogenesis, cause death of sperm or ova, or otherwise cause severe injury to the genetic material. Further activities intended to be encompassed within the scope of the terms "control" or "controlling" include preventing larvae from developing into mature progeny, modulating the emergence of pests from eggs including deterring oviposition, preventing eclosion, degrading the egg material, suffocation, reducing gut motility, inhibiting the formation of chitin, disrupting mating or sexual communication, and preventing feeding (antifeedant) activity.

As used herein, the terms "repellent" or "repelling" mean that a composition discourages pests from landing or climbing on a surface to which the composition has been applied or incorporated, and/or that the composition encourages pests to move away from a surface to which the composition has been applied or incorporated.

As used herein, a "pesticidal natural oil" is a natural oil or oils, for example derived from plant material, that exhibits pesticidal activity either on its own or in combination with a solvent. As used herein, "pesticidal natural oil" includes other materials derived, extracted or otherwise obtained from natural sources, for example, powdered extracts and the like. A "derivative" is a compound or composition that can be obtained from a natural oil. A "constituent" or "component" is a compound or composition found in a natural oil.

As used herein, "neem oil" refers to oil derived from the seeds, leaves, and bark of *Azadirachta indica*. Methods for obtaining neem oil, azadirachtin extract or other derivatives purified from neem oil are known in the art. One exemplary method for obtaining neem oil is cold pressing.

As used herein, "dry residue activity" refers to compositions that exhibit pesticidal activity and/or prevention of egg emergence after the composition has dried for at least two hours from application before pests are exposed to the dry reside.

As used herein, "prolonged residual activity" refers to compositions that exhibit pesticidal activity and/or prevention of egg emergence up to several days after the composition has been applied to a target surface. In some embodiments, "prolonged residual activity" refers to compositions that exhibit pesticidal activity and/or prevention of egg emergence up to one week, two weeks, three weeks, or more after the composition has dried after being applied to a target surface. Higher prolonged residual pesticidal activity can extend the interval between re-treatments of a target surface necessary to achieve an acceptable level of pest control. In some embodiments, prolonged residual activity refers to compositions that exhibit pesticidal activity and/or prevention of egg emergence up to at least 7 days, 8 days, 9 days, 10 days, 11 days, 12 days, 13 days, 14 days, 15 days, 16 days, 17 days, 18 days, 19 days, 20 days, or 21 days after treatment, meaning that a composition does not need to be re-applied to pests or to surfaces where the pests or their eggs may contact or otherwise be exposed to the composition for at least such period of time.

As used herein, "knockdown" activity refers to the pesticidal activity of a composition as applied directly to a pest.

As used herein, "surface" or "target surface" includes a surface to which a pesticide is applied or is to be applied. Such surfaces may include, for example, a surface where pests are likely to contact or otherwise be exposed to the applied pesticide, to lay their eggs, and/or a surface that has been or is suspected to be infested by pests.

As used herein, "preventing oviposition" means that a composition prevents a pest from laying eggs, and/or decreases the number of eggs typically laid by a pest.

As used herein, the term "stability" means the ability of a composition to retain its pesticidal activity after application to a surface to be treated with insecticide.

The term "carrier" as used herein refers to an inert material, organic or inorganic, with which an active ingredient can be mixed or formulated to facilitate its application, storage, transport, and/or handling, or improve various product characteristics such as its odor. Commonly used carriers include, but are not limited to, ethanol, isopropanol, other alcohols, and water. Exemplary carriers that can be used in some embodiments of the invention include inert carriers listed by the U.S. EPA as a Minimal Risk Inert Pesticide Ingredients (4A), Inert Pesticide Ingredients (4B) or under EPA regulation 40 CFR 180.950, each of which is hereby incorporated herein by reference in its entirety for all purposes, including for example, citric acid, lactic acid, glycerol, castor oil, benzoic acid, carbonic acid, ethoxylated alcohols, ethoxylated amides, glycerides, benzene, butanol, 1-propanol, hexanol, other alcohols, dimethyl ether, and polyethylene glycol.

Some embodiments of the present invention provide compositions and methods useful in the control of a variety of pests. Some embodiments of the present invention can be used to control insects, arachnids, centipedes, millipedes and/or other pests. Some embodiments of the present invention can be used to control sucking and biting pests, including e.g. bed bugs, mosquitoes, ticks, lice, fleas, stink bugs, flies, cockroaches, spiders and/or moths.

In some embodiments, the composition includes a combination of a pesticidal natural oil and a polar aromatic solvent. In some embodiments, the combination of the pesticidal natural oil and the polar aromatic solvent is effective to control pests. In some embodiments, the combination of the pesticidal natural oil and the polar aromatic solvent is effective to prevent eclosion. In some embodiments, the combination of the pesticidal natural oil and the polar aromatic solvent is effective to prevent oviposition. In some embodiments, the combination of the pesticidal natural oil and the polar aromatic solvent exhibits effective knockdown pesticidal activity. In some embodiments, the combination of the pesticidal natural oil and the polar aromatic solvent exhibits prolonged residual pesticidal activity.

In some embodiments, the combination of the pesticidal natural oil and the polar aromatic solvent exhibits markedly improved ability to control pests and/or an expanded range of pesticidal activity as compared with either the pesticidal natural oil or the polar aromatic solvent alone. In some embodiments, a composition including a combination of a pesticidal natural oil and a polar aromatic solvent exhibits improved dry residue pesticidal activity as compared with either the pesticidal natural oil or the polar aromatic solvent used alone. In some embodiments, a composition including a combination of a pesticidal natural oil and a polar aromatic solvent acts to prevent eclosion when used under conditions at which the pesticidal natural oil or the polar aromatic solvent used alone would not prevent eclosion to a significant level. In some embodiments, a composition including a combination of a pesticidal natural oil and a polar aromatic solvent acts to prevent oviposition when used under conditions at which the natural oil or the polar aromatic solvent used alone would not prevent oviposition to a significant level. In some embodiments, a composition including a combination of a pesticidal natural oil and a polar aromatic solvent exhibits improved or more rapid knockdown of a pest as compared with either the pesticidal natural oil or the polar aromatic solvent used alone. In some embodiments, a composition including a combination of a pesticidal natural oil and a polar aromatic solvent exhibits prolonged residual pesticidal activity as compared with either the pesticidal natural oil or the polar aromatic solvent used alone. In some embodiments, a composition including a combination of a pesticidal natural oil and a polar aromatic solvent exhibits prolonged residual egg eclosion prevention activity, while the pesticidal natural oil or the solvent used alone do not exhibit such activity.

In some embodiments, a composition including a combination of a polar aromatic solvent with a pesticidal natural oil shows a lesser degree of repellency than the repellency of the pesticidal natural oil used alone. Under certain experimental conditions described herein, dry residues of exemplary combinations comprising neem oil in combination with a polar aromatic solvent demonstrate significantly less repellency to adult bed bugs than dry residues of neem oil alone, and exhibit comparable levels of repellency when compared with an untreated control. In some embodiments, the combination of a polar aromatic solvent with a pesticidal natural oil appears to mitigate the repellency of the natural oil (that is, the repellency of a target surface treated with the combination is the same as the repellency of the untreated target surface). In some embodiments, the combination of a polar aromatic solvent with a pesticidal natural oil appears to mitigate the repellency and improve the attractancy of the natural oil (that is, a target surface treated with the combination is more attractive than the untreated target surface and/or the treatment flushes pests out of hiding spots and crevices).

Decreasing the repellency of a pesticidal natural oil (or acting as an attractant) can increase the effectiveness of a composition as a pesticide, because pests will remain in an area where the composition has been applied (or can be flushed from hiding areas), rather than moving to untreated areas due to the repellency of the pesticidal natural oil, and thereby avoiding or being otherwise unaffected by the properties of the pesticide. In some cases, applying a product with a high degree of repellency can result in the spread of pests, as the pests move away from the location to which the repellent product has been applied. For example, if there is a localized infestation of pests in a residential dwelling and a repellent product is applied to the area where the infestation is localized, the pests may simply move on and infest other areas of the residential dwelling.

In some embodiments, a pesticidal composition includes two or more natural oils and a polar aromatic solvent. In some embodiments, at least one of the natural oils is a pesticidal natural oil, and at least one of the natural oils is an oil or fragrance selected to decrease the repellency of the one or more pesticidal natural oils in the composition. In some embodiments, the natural oils are selected to provide a composition that has an odor to humans that is more pleasant than the odor of the pesticidal natural oil alone, i.e. the natural oil is an additive that masks the odor of the pesticidal natural oil.

In some embodiments, the polar aromatic solvent is a ketone. In some embodiments, the polar aromatic solvent is a simple ketone. In some embodiments, the polar aromatic solvent is acetophenone. In some embodiments, the polar aromatic solvent is an alcohol, an aldehyde, an ester, or a carboxylic acid. In some embodiments, the polar aromatic solvent is an aryl alcohol, an aryl-alkyl alcohol, an aryl aldehyde, an aryl ketone, an aryl-alkyl ketone, an aryl-aryl ketone, an aryl carboxylic acid, an aryl-alkyl ester, an aryl-aryl ester, an aryl-alkyl ether, an aryl-aryl ether and/or a combination thereof.

In some embodiments, the polar aromatic solvent has the general structure

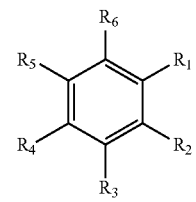

(I)

wherein $R_1$ can be:

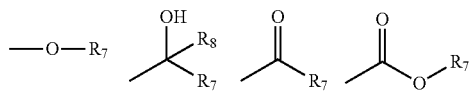

and wherein $R_2$, $R_3$, $R_4$, $R_5$ and $R_6$ can independently be —H, or an alkyl group, alkenyl group or alkynyl group, including e.g. a methyl, ethyl, propyl, isopropyl, butyl, or pentyl group or the like, or an —OH group or a halo functional group, or an alkyl, alkenyl or alkynyl group including an alcohol, halo or other polar functional group; and wherein $R_7$ and $R_8$ can independently be —H or an alkyl group, including e.g. a methyl, ethyl, propyl, isopropyl, butyl, or pentyl group or the like, or an aromatic group. In some embodiments, $R_7$ and/or $R_8$ can have other substituents. In some embodiments $R_2$, $R_3$, $R_4$, $R_5$ and/or $R_6$ can have other substituents. Other polar aromatic compounds could be used in some embodiments.

In some embodiments, the polar aromatic solvent is benzyl alcohol, 3,4-dimethylbenzyl alcohol, alpha-4-dimethylbenzyl alcohol, 2-phenyl-2-propanol, 1-phenylethanol, benzaldehyde, methylcyclohexylketone, cyclohexanone, p-tolualdehyde, 2-hydroxy-5-methyl benzaldehyde, acetophenone, 4'-hydroxyacetophenone, 4'-methylacetophenone, 2'-hydroxyacetophenone, 2',4'-dimethylacetophenone, 3',4'-dimethylacetophenone, propiophenone, 4'-methylproppiophenone, butyrophenone, isobutryophenone, valerophenone, 4'-hydroxyvalerophenone, cyclohexyl phenyl ketone, hexanophenone, 2,2',4,4'-tetrahydroxybenzophenone, t-tert-butylcyclyhexylacetate, benzoic acid, 4-hydroxy benzoic acid, 4-hydroxy-3-methyl benzoic acid, ethyl benzoate, isobutyl benzoate, benzyl benzoate, propyl-4-hydroxybenzoate, phenol, benzyl methyl ether, butyl phenyl ether, trans-anethole, dibenzyl ether, diphenyl ether, and/or a combination thereof.

In some embodiments, the polar aromatic solvent is replaced by an alkyl alcohol. In some embodiments, the solvent is 2-ethyl-1-hexanol, 1-nonanol, 2-butyl-1-octanol, 2-hexyl-1-decanol, 1-dodecanol, 2-octanol, 1-decanol, 2-propanol (IPA), cyclohexanol, and/or a combination thereof.

In some embodiments, compositions including a pesticidal natural oil and a polar aromatic solvent exhibit significantly improved stability and dry residue pesticidal activity as compared to the dry residue pesticidal activity of the pesticidal natural oil or the polar aromatic solvent alone. In one embodiment, the addition of acetophenone or other polar aromatic organic solvent to neem oil or a component or derivative of neem oil provides a composition with significantly improved stability and dry residue pesticidal activity as compared with neem oil or its components or derivatives alone, and as compared with the dry residue pesticidal activity of the solvent alone.

In some embodiments, compositions including a pesticidal natural oil and a polar aromatic solvent prevent egg emergence (i.e. prevent eclosion). In some embodiments, compositions including a pesticidal natural oil and a polar aromatic solvent exhibit prolonged egg eclosion prevention activity.

In some embodiments, a composition including a combination of a pesticidal natural oil and a polar aromatic solvent exhibits improved prevention of oviposition as compared with either the pesticidal natural oil or polar aromatic solvent alone.

In some embodiments, a composition including a combination of a pesticidal natural oil and a polar aromatic solvent exhibits improved or more rapid knockdown of pests as compared with either the pesticidal natural oil or polar aromatic solvent alone.

In some embodiments, compositions including a pesticidal natural oil and a polar aromatic solvent exhibit both improved or more rapid knockdown of pests as compared with either the pesticidal natural oil or the polar aromatic solvent used alone, and also prolonged dry residual pesticidal activity.

In some embodiments, the pesticidal natural oil is neem oil or a component or derivative thereof. In other embodiments, the pesticidal natural oil is neem oil, clove oil, peppermint oil, cinnamon oil, thyme oil, oregano oil, garlic oil, anise oil, geranium oil, lime oil, lavender oil, components or derivatives thereof—including for example geraniol derived from geranium oil and eugenol derived from clove oil—or a combination of the foregoing. Table 1 presents a summary of major chemical constituents (i.e. components) of some pesticidal natural oils. In some embodiments, the pesticidal natural oil is any oil that includes one or more constituents common to two or more of the pesticidal natural oils listed in Table 1 (i.e. neem oil, clove oil, peppermint oil, cinnamon oil, thyme oil, oregano oil, garlic oil, anise oil, geranium oil, lime oil, lavender oil), including, but not limited to, thymol (found in oregano oil and thyme oil), p-cymene (found in oregano oil and thyme oil), 1,8-cineole (found in thyme oil and peppermint oil), eugenol (found in clove oil and cinnamon oil), limonene (found in cinnamon, peppermint, and lime oil), alpha-pinene (found in cinnamon oil, geranium oil, and lime oil), carvacrol (found in oregano oil, thyme oil, and clove oil), gamma-terpinene (found in oregano oil and lime oil), geraniol (found in thyme oil and geranium oil), alpha-Terpineol (found in thyme oil and anise oil), beta-caryophyllene (found in clove oil, cinnamon oil, and peppermint oil) and linalool (found in thyme oil, cinnamon oil and geranium oil, amongst others). In other embodiments, the pesticidal natural oil is any oil having as a constituent one of the following compounds, or a combination of the following compounds: azadirachtin, nimbin, nimbinin, salannin, gedunin, geraniol, geranial, gamma-terpinene, alpha-terpineol, beta-caryophyllene, terpinen-4-ol, myrcenol-8, thuyanol-4, benzyl alcohol, cinnamaldehyde, cinnamyl acetate, alpha-pinene, geranyl acetate, citronellol, citronellyl formate, isomenthone, 10-epi-gamma-eudesmol, 1,5-dimethyl-1-vinyl-4-hexenylbutyrate, 1,3,7-octatriene, eucalyptol, camphor, diallyl disulfide, methyl allyl trisulfide, 3-vinyl-4H-1,2 dithiin, 3-vinyl-1,2 dithiole-5-cyclohexane, diallyl trisulfide, anethole, methyl chavicol, anisaldehyde, estragole, linalyl acetate, geranial, beta-pinene, thymol, carvacrol, p-cymene, beta-myrcene, alpha-myrcene, 1,8-cineole, eugenol, limonene, alpha-pinene, menthol, menthone, and linalool.

TABLE 1

Chemical Constituents of Pesticidal Natural Oils

| Essential oil | Chemical Constituent | Reference |
|---|---|---|
| Oregano oil | Thymol; Carvacrol; p-cymene; gamma-terpinene; alpha-terpinene; linalool | Vokou; Toncer |
| Neem oil | Azadirachtin; Nimbin; Nimbinin; Salannin; Gedunin | Schmutterer |
| Thyme oil | Thymol; Geraniol; Carvacrol; Linalool; alpha-Terpineol; p-Cymene; 1,8-Cineole; terpinen-4-ol; Myrcenol-8; Thuyanol-4; myrcene; gamma-terpinene; alpha-terpinene | Thompson; Granger & Passet; Shabnum & Wagay |
| Clove oil | Eugenol; benzyl alcohol; carvacrol; thymol; cinnamaldehyde; beta-caryophyllene | Chaieb |
| Cinnamon oil | Linalool; cinnamyl acetate; beta-caryophyllene; alpha-pinene; eugenol; cinnamaldehyde; limonene | Kaul; Simic |
| Geranium oil | Geraniol; linalool; geranyl acetate; citronellol; citronellyl formate; isomenthone; alpha-pinene; 10-epi-gamma-eudesmol | Rajeswara Rao |
| Peppermint oil | Menthol; Menthone; 1,8-Cineole; Methyl acetate; Limonene; beta-caryophyllene | Gochev; Clark & Menary |
| Lavender oil | 1,5-Dimethyl-1-vinyl-4-hexenylbutyrate; 1,3,7-Octatriene; eucalyptol; camphor | Hui; Shellie, Mondello, Marriott, & Dugo |
| Garlic oil | Diallyl disulfide; Methyl allyl trisulfide; 3-Vinyl-4H-1,2 dithiin; 3-Vinyl-1,2 dithiole-5-cyclohexane; Diallyl trisulfide | Kimbaris; Avato |
| Anise oil | Anethole; methyl chavicol; anisaldehyde; estragole; alpha-Terpineol; linalool | Santos; Arslan |
| Lime oil | d-limonene; linalyl acetate; beta-myrcene; linalool; alpha-pinene; geranial; beta-pinene; gamma-terpinene | Vasudeva & Sharma; Lota, M.-L. |

Table 2 presents a summary of known pesticidal activities (including insecticidal, acaricidal, ovicidal, larvicidal, reducing growth rate, and pupation inhibiting activities) of constituents of some pesticidal natural oils. In some embodiments, the pesticidal natural oil is any oil or any constituent that comprises a significant quantity (i.e. an amount of the constituent sufficient to provide the natural oil with pesticidal activity) of one or more constituents possessing insecticidal activity. In some embodiments, the pesticidal natural oil is any oil that comprises a significant quantity (i.e. an amount of the constituent sufficient to provide the natural oil with pesticidal activity) of one or more of the constituents listed in Table 2, namely thymol, p-cymene, eugenol, cinnamaldehyde, linalool, cinnamyl acetate, menthol, d-limonene, anethole, carvacrol, alpha-pinene, geraniol, 1,8-cineole, myrcene, anisaldehyde, alpha-terpineol, alpha-terpinene, gamma-terpinene, terpinen-4-ol, and beta-myrcene. In some embodiments, the constituent known to possess insecticidal activity is a terpene, for example, azadirachtin. In some embodiments, the constituent of the pesticidal natural oil is present in an amount greater than or equal to about 0.1%, greater than or equal to about 0.5% or greater than or equal to about 1% by weight in the pesticidal natural oil.

TABLE 2

Known Pesticidal Activities of Chemical Constituents of Pesticidal Natural Oils

| Compound | Activity | Reference |
|---|---|---|
| Thymol | Insecticidal activity - M. domestica & S. litura | Lee |
| Thymol | Insecticidal activity - D. melanogaster | Franzios |
| Thymol | Insecticidal activity - C. pipiens molestus | Traboulsi |
| p-Cymene | Antifeedant activity - pales weevil | Salom |
| Eugenol | Antifeedant activity - P. Brassicae larvae | Jones & Firn |
| Eugenol | Insecticidal activity - P. capitis | Yang et al. (2003) |
| Eugenol | Insecticidal activity - A. dirus mosquitoes | Trongtokit |
| Eugenol | Acaricidal activity - D. farina & D. pteronyssinus | Kim, Kim, & Ahn |
| Cinnamaldehyde | Insecticidal activity - C. quinquefasciatus & A. tessellatus | Samarasekera |
| Cinnamaldehyde | Acaricidal activity - termites | Chang & Cheng |
| Linalool | Insecticidal activity - P. humanus capitis | Yang et al. (2005) |
| Linalool | Acaricidal activity - P. cuniculi | Perrucci |
| Linalool | Antifeedant activity - S. litura | Hummelbrunner, & Isman |
| Linalool | Reduce growth rate - B. germanica | Karr & Coats |
| Cinnamyl acetate | Insecticidal activity - P. humanus capitis | Yang et al. (2005) |
| Menthol | Insecticidal activity - Tracheal mites | Ellis & Baxendale |
| Menthol | Inhibit pupation - P. saucia | Harwood, Modenke, & Berry |
| Menthol | Insecticidal activity - T. castaneum & C. maculatus | Tripathi |
| d-limonene | Insecticidal activity - M. domestica, D. virgifera, S. litura, some cockroaches | Lee (1997); Don-Pedro |
| d-limonene | Reduce growth rate - B. germanica | Karr & Coats |
| Anethole | Insecticidal activity - B. germanica | Chang & Ahn |
| Anethole | Insecticidal activity - house fly | Fuhremann, et al. |
| Carvacrol | Insecticidal activity - A. simplex | Hierro, et al. (2004) |
| Carvacrol | Insecticidal activity - C. pipiens molestus | Traboulsi |
| alpha-pinene | Insecticidal activity - C. pipiens molestus | Traboulsi |
| Geraniol | Insecticidal activity - A. simplex | Hierro |
| 1,8-Cineole | Acaricidal activity - house dust mites | Miresmailli, Bradbury & Isman |
| 1,8-Cineole | Reduce growth rate - Coleopteran sp. | Obeng-Ofori & Reichmuth |
| 1,8-Cineole | Insecticidal activity - T. castaneum | Tripathi, Prajanpati, Aggarwal, & Kumar |
| Myrcene | Reduce growth rate - B. germanica | Karr & Coats |

TABLE 2-continued

Known Pesticidal Activities of Chemical Constituents of Pesticidal Natural Oils

| Compound | Activity | Reference |
|---|---|---|
| Anisaldehyde | Insecticidal activity - hoiuse fly | Marcus & Lichtenstein |
| alpha-Terpineol | Reduce growth rate - B. germanica | Karr & Coats |
| alpha-Terpineol | Antifeedant activity - S. litura | Hummelbrunner & Isman |
| alpha-Terpinene | Larvicidal activity - A. aegypti & A. albopictus | Cheng (2009) |
| gamma-terpinene | Larvicidal activity - A. aegypti & A. albopictus | Cheng (2009) |
| gamma-terpinene | Larvicidal activity - A. fabae & S. littoralis | Abbassy |
| Terpinen-4-ol | Larvicidal activity - A. fabae & S. littoralis | Abbassy |
| p-cymene | Larvicidal activity - A. aegypti & A. albopictus | Cheng (2009) |
| beta-myrcene | Larvicidal activity - A. aegypti & A. albopictus | Cheng (2009) |

Other oils that can be used, alone or in combination, as additives in some embodiments of the present invention can be derived from plant, animal or mineral sources, or be synthetic. Such oils may be added as a carrier and/or for various other purposes, including but not limited to, improving odor characteristics (e.g. acting as an odor-masking agent), improving properties of another oil used as an active ingredient, decreasing repellency, acting as a pesticide, and/or improving other properties of the formulation. Such oils include, but are not limited to, castor oil, orange oil, citrus oil, cedar oil, linseed oil, soybean oil, licorice oil, mint oil, sweet birch oil, canola oil, jojoba oil, lavandin oil, mustard seed oil, coconut oil, eue oil, tulsi oil, almond oil, cottonseed oil, corn oil, germanium oil, sesame oil, tung oil, rosemary oil, basil oil, fennel oil, ginger oil, grapefruit oil, mandarin oil, pepper oil, rose oil, tangerine oil, tea tree oil, tea seed oil, pine oil, cardamom oil, *cassia* oil, celery oil, cognac oil, dill weed oil, juniper oil, guiacwood oil, parsley oil, pimento leaf oil, apricot oil, *origanum* oil, betel leaf oil, ajowan oil, chilly seed oil, cubeb oil, curry oil, frankincense oil, ginger grass oil, heeng oil, jamrosa oil, kalaunji oil, citronella oil, linaloe berry oil, ban tulasi oil, bursera oil, lemon balm oil, karanja oil, nepetalactone oil, mink oil, limba pine oil, litsea cubeba oil, lovage oil, manuca oil, marjoran oil, milfoil oil, myrrh oil, myrtle oil, neroli oil, niauli oil, cumin seed oil, cyperiol oil, gereniol oil, grape seed oil, hinoki oil, laurel berry oil, lichen oil, mace oil, mango ginger oil, *mentha* pipereta oil, paprika oil, vetivert oil, wheat germ oil, macassar oil, *mentha* citreta oil, musk melon oil, nar kachur oil, palmarosa oil, patchouli oil, pomegranate oil, pumpkin oil, tomar seed oil, cananga oil, avocado oil, safflower oil, abies alba needle oil, ambrette seed oil, amyris oil angelica root oil, *artemisia* oil, estragon oil, fir needle oil, galangal oil, galbanum oil, olibanum oil, palmarosa oil, patchouli oil, birch oil, cajeput oil, calamus oil, cedarwood oil, wintergreen oil, carrot oil, *costus* oil, cypress oil, davana oil, dwarf pine needle oil, elemi oil, guajac oil, hop oil, hyssop oil, chamomile oil, jasmine oil, larch oil, rosewood oil, oil, sassafras oil, tagetes oil, *thuja* oil, valerian oil, verbena oil, vervain oil, vetiver oil, wormwood oil, ylang ylang oil, olive oil, evening primrose oil, hazelnut oil, grape core oil, peach core oil, walnut oil, sunflower oil, sandalwood oil, turmeric oil, nutmeg oil, soy oil, vegetable oils, menthol oil, eucalyptol, camphor oil, cedar leaf oil, laurel leaf oil, balsam oil, bay oil, *capsicum* oil, spearmint oil, caraway seed oil, lemon eucalyptus oil, lemongrass oil, sage oil, pennyroyal oil, bergamot oil, mineral oil, other natural or essential oils, or combinations thereof.

In some embodiments, the additive is an odor-masking agent or compound. In some embodiments, the odor-masking agent is vanilla extract, wintergreen oil, spearmint oil, clove oil, lemongrass oil, and/or a combination thereof.

In some embodiments, the additive can be a second pesticidal natural oil or other material having pesticidal activity, including for example cinnamon oil, thyme oil, clove oil, clove leaf oil, clove bud oil, eugenol, lime oil, oregano oil, thyme oil, mint oil (including spearmint or peppermint oil), or the like.

In some embodiments, the additive can be an odor-neutralizing agent. In some embodiments, the odor-neutralizing agent can be an odor-absorbent material. In some embodiments, the additive is zeolite and/or other natural or synthetic odor absorbent material.

Derivatives and/or components of neem oil that can be used in embodiments of the present invention include, but are not limited to, neem oil, palmitoleic acid, alpha-linolenic acid, stearic acid, palmitic acid, oleic acid, linoleic acid, campesterol, beta-sitosterol, stigmasterol, azadirachtin, meliantriol, melianone, gedunin, amoorastatin, vepinin, marrangin, vilasinin, nimbin, nimbolide, nimbolinin, ohchinolide, nimbolinin, salannin, meliacarpin, meliaquinal, nimbandiol, nimbinene, nimbocinone, kulactone, limocinol, limocinone, nimolinone, azadirachnol, or other triterpenoids, azadirone, azadiradione, azadirachtol, epoxyazadiradione, other compounds derived from neem, related to neem, combinations thereof, and their active derivatives.

Derivatives and/or components of other pesticidal natural oils that can be used in some embodiments of the present invention include, but are not limited to, thymol, p-cymene, 1,8-cineole, eugenol, limonene, carvacrol, menthol, alpha-pinene, linalool, menthone, carvacrol, gamma-terpinene, geraniol, alpha-terpineol, beta-caryophyllene, linalool, gedunin, geranial, terpinen-4-ol, myrcenol-8, thuyanol-4, benzyl alcohol, cinnamaldehyde, cinnamyl acetate, geranyl acetate, citronellol, citronellyl formate, isomenthone, 10-epi-gamma-eudesmol, 1,5-dimethyl-1-vinyl-4-hexenylbutyrate, 1,3,7-octatriene, eucalyptol, camphor, diallyl disulfide, methyl allyl trisulfide, 3-vinyl-4H-1,2 dithiin, 3-vinyl-1,2 dithiole-5-cyclohexane, diallyl trisulfide, anethole, methyl chavicol, anisaldehyde, estragole, linalyl acetate, beta-pinene, beta-myrcene, alpha-myrcene, menthol, and other compounds derived from pesticidal natural oils, combinations thereof, and their active derivatives.

In some embodiments, a surfactant is used in preparing pesticidal compositions or pest control agents. Suitable surfactants can be selected by one skilled in the art. Examples of surfactants that can be used in some embodiments of the present invention include, but are not limited to, ethoxylated castor oil, sodium lauryl sulfate, saponin, ethoxylated alcohols, ethoxylated fatty esters, alkoxylated glycols, ethoxylated fatty acids, carboxylated alcohols, carboxylic acids, fatty acids, ethoxlylated alkylphenols, fatty esters, sodium dodecylsulfide, other fatty acid-based surfactants, other natural or synthetic surfactants, and combinations thereof. In some embodiments, the surfactant(s) are non-ionic surfactants. In some embodiments, the surfactant(s) are ionic surfactants. The selection of an appropriate surfactant depends upon the relevant applications and conditions of use, and appropriate surfactants are known to those skilled in the art.

In some embodiments, a pesticidal composition includes a suitable carrier. A suitable carrier can be selected by one skilled in the art, depending on the particular application desired and the conditions of use of the composition. Commonly used carriers include ethanol, isopropanol, other alcohols, water and other inert carriers listed by the EPA as a Minimal Risk Inert Pesticide Ingredients (4A), Inert Pesticide Ingredients (4B) or under EPA regulation 40 CFR 180.950, each of which is hereby incorporated herein in its entirety for all purposes including for example, citric acid, lactic acid, glycerol, castor oil, benzoic acid, carbonic acid, ethoxylated alcohols, ethoxylated amides, glycerides, benzene, butanol, 1-propanol, hexanol, other alcohols, dimethyl ether, and polyethylene glycol.

Some embodiments of the present invention include combinations of a pesticidal natural oil (and/or components and/or derivatives thereof) with a polar aromatic solvent and one or more other natural oils (plant, animal or mineral derived), synthetic oils, and/or chemical derivatives of any of the foregoing.

In some embodiments, a pesticidal composition comprises a pesticidal natural oil at a concentration of between 0.25% and 99.3% by weight, including any concentration therebetween e.g. 0.3%, 0.4%, 0.5%, 0.6%, 0.7%, 0.8%, 0.9%, 1%, 2%, 5%, 7.5%, 10%, 15%, 20%, 25%, 30%, 35%, 40%, 45%, 50%, 55%, 60%, 65%, 70%, 75%, 80%, 85%, 90%, 95%, 98% or 99% by weight; and a polar aromatic solvent at a concentration between 0.7% and 99.75% by weight, including any concentration therebetween e.g. 0.8%, 0.9%, 1.0%, 1.2%, 1.4%, 1.6%, 1.8%, 2%, 3%, 4%, 5%, 7.5%, 10%, 15%, 20%, 25%, 30%, 35%, 40%, 45%, 50%, 55%, 60%, 65%, 70%, 75%, 80%, 85%, 90%, 95%, 98% or 99% by weight. In some embodiments, the polar aromatic solvent is present at a concentration between 0.13 mol/kg and 8.3 mol/kg or any value therebetween, e.g. 0.2, 0.4, 0.6, 0.8, 1.0, 1.5, 2.0, 2.5, 3.0, 3.5, 4.0, 4.5, 5.0, 5.5, 6.0, 6.5, 7.0, 7.5, or 8.0 mol/kg.

In some embodiments, a pesticidal composition is provided in which the weight ratio of polar aromatic solvent to pesticidal natural oil is in the range of 1.5:1 to 7:1, or any range therebetween including e.g. 2:1, 2.5:1, 3:1, 4:1, 5:1, or 6:1.

One exemplary composition according to one embodiment includes neem oil or a component or derivative thereof, acetophenone or another polar aromatic solvent, and optionally includes a surfactant, additional insect controlling compounds and/or additional natural oils or other products to add fragrance, decrease repellency, or extend the range of insects susceptible to the composition. In one embodiment, such a composition includes neem oil (or a derivative thereof) at a concentration between 0.1% and 99% by weight, including any concentration therebetween e.g. 0.2%, 0.25%, 0.3%, 0.4%, 0.5%, 0.6%, 0.7%, 0.8%, 0.9%, 1%, 2%, 5%, 7.5%, 10%, 15%, 20%, 25%, 30%, 35%, 40%, 45%, 50%, 55%, 60%, 65%, 70%, 75%, 80%, 85%, 90%, 95%, 98% or 99% by weight; and acetophenone at a concentration between 0.7% and 99.75% by weight (between 0.13 mol/kg and 8.3 mol/kg or any value therebetween, e.g. 0.2, 0.4, 0.6, 0.8, 1.0, 1.5, 2.0, 2.5, 3.0, 3.5, 4.0, 4.5, 5.0, 5.5, 6.0, 6.5, 7.0, 7.5, or 8.0 mol/kg), including any concentration therebetween e.g. 0.8%, 0.9%, 1.0%, 1.2%, 1.4%, 1.6%, 1.8%, 2%, 3%, 4%, 5%, 7.5%, 10%, 15%, 20%, 25%, 30%, 35%, 40%, 45%, 50%, 55%, 60%, 65%, 70%, 75%, 80%, 85%, 90%, 95%, 98% or 99% by weight. The exemplary composition optionally includes one or more surfactants, other pesticidal ingredients, stabilizers, carriers, diluents, or other non-pesticidal ingredients, and/or other natural oils.

In one exemplary embodiment, a pesticidal composition includes a combination of neem oil at a concentration of 5.5% by weight, acetophenone at a concentration of 15.5% by weight, natural oils (lemongrass oil, spearmint oil, clove oil, and wintergreen oil) at 8% or 3.4% by weight and a surfactant at a concentration of 5.0% by weight. In one exemplary embodiment, a pesticidal composition includes a combination of neem oil at a concentration of 5.5% by weight, acetophenone at a concentration of 18.25% by weight, and 1.25% ethoxylated castor oil by weight.

Exemplary formulations according to one exemplary embodiment comprising neem oil as the pesticidal natural oil and acetophenone as the solvent were shown to demonstrate improved dry residue pesticidal activity as compared with neem oil alone when neem oil and acetophenone are present at a concentration of at least 0.55% and 1.55% by weight, respectively.

Formulations according to another exemplary embodiment were found to demonstrate improved dry residue prevention of egg eclosion as compared with neem oil alone when neem oil and acetophenone were present at concentrations of at least 0.25% and 0.7% by weight, respectively.

Some embodiments of the present invention can be used to control pests such as arthropods, including insects and arachnids. Exemplary embodiments of the present invention have been demonstrated to have efficacy against arthropods including insects, spiders, centipedes and millipedes, including bed bugs, German cockroaches (*Blattella germanica*), Smoky Brown cockroaches (*Periplaneta fuliginosa*), American cockroaches (*Periplaneta americana*), cat fleas (*Ctenocephalides felis*), fire ants (*Solenopsis Invicta*), black carpenter ants (*Camponotus pennsylvanicus*), pavement ants (*Tetramorium caespitum*), field ants (*Formica* sp.), moisture ants (*Lasius* sp.), wood ants (*Formica rufa*), house flies (*Musca domestica*), bottle flies (*Lucilia sericata*), giant silverfish (*Ctenolepisma longicaudata*), firebrats (*Thermobia domestica*), bean aphids (*Aphis fabae*), pea aphids (*Acyrthosiphon pisum*), termites (*Reticulitermes flavipes*), granary weevils (*Sitophilus granarius*), maize weevils (*Sitophilus zeamais*), confused flour beetles (*Tribolium confusum*), rusty grain beetles (*Cryptolestes ferrugineus*), dust mites (*Dermatophagoides farinae*), millipedes (*Cylindroiulus caeruleocinctus*), centipedes (*Strigamia aluminata*), sowbugs (*Oniscus asellus*), orabatid mites (*Haplozetes* sp.), house crickets (*Acheta domestica*), black widow spiders (*Latrodectus mactans*), brown recluse spiders (*Loxosceles reclusa*), and pharaoh ants (*Monomorium pharaonis*). Exemplary embodiments of the present invention have been demonstrated to have efficacy in preventing eclosion of arthropod eggs, including bed bug eggs and cockroach eggs. Some embodiments of the present invention can also be used to control insects, arachnids, centipedes, millipedes, or other arthropods upon which they are expected to be effective based on their demonstrated activity, including, but not limited to, whiteflies, mosquitoes, other species of flies, other species of aphids, other species of silverfish, lice, stink bugs, moths, beetles, lace bugs, whiteflies, green peach aphids, western floral thrips, diamondback moths, leafminers, grasshoppers, crickets, locusts, leafhoppers, planthoppers, psyllids, scale insects, midges, fruit flies, earworms, bollworms, armyworms, budworms, hornworms, milkweed bugs, mealy bugs, weevils, botflies, face flies, sawflies, rice bugs, coffee bugs, vegetable bugs, corn borers, horn flies, blowflies, sowbugs, pillbugs, mites, centipedes and millipedes. Exemplary embodiments of the present invention have been demonstrated to have efficacy against arachnids including cellar spiders, ticks, black widow spiders and brown recluse spiders. Some embodiments of the present invention can also be used to control other arachnids upon which they are expected to be effective, including, but not limited to, scorpions and other species of spiders. This disclosure is intended to encompass uses against all of the above, as well as uses against other pests, including other insects and arachnids, and other organisms including fungi, bacteria, viruses, and nematodes.

In some embodiments, the pesticidal compositions described herein are effective to kill and/or control pests and/or prevent or reduce oviposition and/or prevent or reduce eclosion of their eggs. In some embodiments, the pesticidal compositions described herein exhibit effective knockdown pesticidal activity, exhibit effective dry residue pesticidal activity, and/or exhibit effective prolonged residual pesticidal activity.

In some embodiments, the pesticidal compositions described herein are effective to kill and/or control pests and/or prevent oviposition and/or prevent eclosion of their eggs, or exhibit improved knockdown of a pest, dry residue pesticidal activity, and/or prolonged residual pesticidal activity, when the concentration of each of the pesticidal natural oil and the polar aromatic solvent is below a level at which the pesticidal natural oil and the polar aromatic solvent used alone would be effective to achieve the same function. In some embodiments, the pesticidal compositions described herein exhibit a synergistic pesticidal effect as compared with the activity the pesticidal natural oil or the polar aromatic solvent used alone. In some embodiments, the pesticidal compositions described herein exhibit significantly improved pesticidal effect as compared with the activity of the pesticidal natural oil or the polar aromatic solvent used alone at the same concentration.

Some embodiments of the present invention can be used to control pests that affect humans and non-human mammals including bed bugs, cockroaches, lice, fleas, ticks, mites, and scabies. Some embodiments of the present invention can be used to control pests that affect plants or agriculture, such as aphids or nematodes. In some embodiments, any of the compositions described above may be used in any situation in which a neem oil-based insect control agent is currently employed.

In some embodiments, any of the compositions described above are formulated in a deliverable form suited to a particular application. Deliverable forms that can be used in accordance with embodiments of the present invention include, but are not limited to, liquids, emulsions, solids, waxes, dusts, fumigants, aqueous suspensions, oily dispersions, pastes, powders, dusts, emulsifiable concentrates, aerosol sprays, wood fillers, varnishes, wood treatments or furniture oils, detergents, drywall mixtures, fumigating candles, caulking compositions, crack and crevice fillers, sealing agents, and mattress and mattress cover treatments. Suitable deliverable forms can be selected and formulated by those skilled in the art using methods currently known in the art.

Some embodiments of the present invention demonstrate effective insect control activity on surfaces where pest products are commonly employed, including, but not limited to, carpet, mattresses, wood, and fabrics. In some embodiments, any of the compositions described above are applied to surfaces inside a household, residence or building. In some embodiments, any of the compositions described above are applied to mattresses, sheets, fabrics, travel bags/ suitcases, carpets, painted or unpainted hard surfaces, wood, flooring, furniture and/or buildings. In some embodiments, any of the compositions described herein are applied outdoors or to plants or agricultural areas and/or inside or outside structures.

Some embodiments are effective as an insect control agent against insects resistant to pyrethrins (eg. pyrethrum) and pyrethroids (eg. deltamethrin, bifenthrin, λ-cyhalothrin, etc.). In some embodiments, the pyrethrin-resistant insect is a bed bug (*Cimex lectularius* L.).

Some embodiments provide methods of using any of the compositions described above to control populations of bed bugs and/or other insects, arachnids and/or other arthropods. Some embodiments provide a method of killing and/or controlling pests and/or preventing oviposition and/or eclosion of their eggs by applying any of the compositions described herein directly to the pests or to surfaces where the pests or their eggs may contact the composition. Some embodiments provide a method of killing and/or controlling pests and/or preventing oviposition and/or eclosion of their eggs by applying any of the compositions described herein to surfaces so that the pests and/or their eggs will be exposed to the compositions, including to vapors of the compositions. In some embodiments, the pests are insects and/or arachnids and/or centipedes and/or millipedes. In some embodiments, the insects are of the orders Hemiptera, Hymenoptera, Blattodea, Isoptera, Diptera, Lepidoptera, Thysanoptera, Thysanura, Coleopteran, Siphonaptera, Phthiraptera, Psocidae, Dermaptera, Orthoptera. In some embodiments, the pests are bed bugs or cockroaches.

In some embodiments, the methods of use of any of the compositions described herein include combination with natural oils for direct application, dilution with an appropriate carrier for delivery as a ready-to-use spray, or in a concentrated form to be diluted and applied. Other methods of use include, but are not limited to, use as a wood treatment or furniture oil, as a laundry detergent, as a gel or paste which can be applied to a target location, as an oily emulsion, as a dust formulation, as a component in drywall mixture, as a crack or crevice filler or other sealing agent, as a foam, as a component in caulking compositions, as a fumigating mist or candle, as an aerosol or aerosol bomb, or in a formulation employed for treating mattresses or mattress covers. In some embodiments, any of the compositions described above are used for indoor domestic or commercial uses in dispersible forms against a range of pests. Some embodiments of the present invention can be used in dispersible forms in agricultural or other outdoor settings to control pests.

In some embodiments, the compositions described herein exhibit prolonged residual pesticidal activity, enabling a period of time to pass between re-treatment of target surfaces. In one embodiment, pests are killed or controlled, and/or oviposition and/or eclosion are prevented by applying any of the compositions described herein directly to the pests or to surfaces where the pests or their eggs may contact or otherwise be exposed to the composition. A period of time greater than about a week, e.g. 7 days, 8 days, 9 days, 10 days, 11 days, 12 days, 13 days, 14 days, 15 days, 16 days, 17 days, 18 days, 19 days, 20 days, or 21 days or longer is allowed to pass. Then any of the compositions described herein are re-applied to the pests or to surfaces where the pests or their eggs may contact or otherwise be exposed to the composition.

Formulations according to some embodiments can be prepared in any suitable manner. Some embodiments of the present invention provide methods for preparing pesticidal formulations comprising mixing a pesticidal natural oil and/or a component and/or a derivative thereof and a polar aromatic solvent. In some embodiments, the pesticidal formulation is prepared by heating one or more pesticidal natural oils (or component or derivative thereof) in a water bath before any further components of the formulation are added. The surfactant is added to the pesticidal natural oil, and then one or more solvents are added to the pesticidal natural oil, allowing the solvent to solvate the oil before addition of other ingredients. In some embodiments in which the pesticidal natural oil is neem oil, the formulation is prepared by warming neem oil to a temperature of 25-30° C. before any further components of the formulation are added. The solvent is then added to the oil, allowing the solvent to solvate the oil before addition of other ingredients. Optionally, a surfactant and/or other ingredients (which may include additional natural oils or other pesticides) are then added. In some embodiments, a surfactant is added prior to addition of the solvent. Once all ingredients are completely solvated, they may optionally be combined with an appropriate amount of a conventional diluent and/or additional solvent (including different types of solvents). Other carriers, solvents, surfactants, pseticides, fragrances or odor neutralizers may optionally be added. Appropriate preservatives or stabilizers may optionally be added. Materials that encapsulate, hold, transport, delay release or otherwise improve delivery may optionally be added.

EXAMPLES

Embodiments of the present invention are further described with reference to the following examples, which are intended to be illustrative and not limiting.

In the examples that follow, the neem oil used was cold pressed neem seed oil ("C.P. neem oil").

Example 1—Dry Residue Pesticidal Activity

'Solution A' containing neem oil at 5.5% by weight, 15.5% acetophenone by weight, 8% natural oils (lemongrass oil, spearmint oil, clove oil, and wintergreen oil) by weight, and 5.0% ethoxylated castor oil by weight was prepared with isopropyl alcohol (isopropanol) as a carrier diluent. A serial dilution was performed, comprising 100% Solution A, 50% Solution A in isopropanol, 25% Solution A in isopropanol, and 10% Solution A in isopropanol. 1.0 mL of each solution was applied to 90-millimeter filter paper substrates in petri dishes. Substrates were allowed to air dry for two hours, then were infested with adult bed bugs (approximately half male and half female). Replicates of each treatment group and of a negative Control Group were tested concurrently. Mortality was observed at specified intervals after infestation. Adult bed bugs were counted dead if they were unresponsive when stimulated.

The percentage of dead adult bed bugs was measured at 1-, 2-, 4-, 8-, 12-, 24-, 48-, 72-, and 480-hour intervals after infestation and compared against controls. The data collected are summarized in Table 3. At levels as low as 0.55% neem oil and 1.55% acetophenone by weight the combination demonstrated improved insecticidal activity over an untreated control group. No insecticidal activity, relative to a control, was observed at concentrations of 0.055% neem oil and 0.155% acetophenone by weight.

TABLE 3

Dry Residue Pesticidal Activity.

|  | Control | 100% | 50% | 25% | 10% | 1% |
|---|---|---|---|---|---|---|
| % Concentration C.P. Neem Oil (by weight) | 0 | 5.5 | 2.75 | 1.375 | 0.55 | 0.055 |
| % Concentration Acetophenone (by weight) | 0 | 15.5 | 7.76 | 3.875 | 1.55 | 0.155 |
| Time (Hours) | | | % Mortality | | | |
| 0 | 0.00 | 0.00 | 0.00 | 0.00 | 0.00 | 0.00 |
| 1 | 0.00 | 2.08 | 0.00 | 0.00 | 0.00 | 0.00 |
| 2 | 0.00 | 8.71 | 2.50 | 0.00 | 0.00 | 0.00 |
| 4 | 0.00 | 41.14 | 15.00 | 2.78 | 0.00 | 0.00 |
| 8 | 0.00 | 90.45 | 50.83 | 5.56 | 0.00 | 0.00 |
| 12 | 0.00 | 97.50 | 65.83 | 8.06 | 0.00 | 0.00 |
| 24 | 0.00 | 100.00 | 100.00 | 43.76 | 2.50 | 0.00 |
| 48 | 2.50 | 100.00 | 100.00 | 73.41 | 5.00 | 0.00 |
| 72 | 2.50 | 100.00 | 100.00 | 85.68 | 14.77 | 0.00 |
| 480 | 16.82 | 100.00 | 100.00 | 97.50 | 70.91 | 11.67 |

Example 2—Dry Residue Pesticide Activity of Various Pesticidal Natural Oils

This example illustrates the dry residual pesticidal activity of formulations containing a variety of pesticidal natural oils as active ingredients. Solutions were prepared by combining 2.5% by weight of the pesticidal natural oil as active ingredient, 2.5% by weight sodium lauryl sulphate, 5.0% by weight solvent (either ethyl lactate or acetophenone as noted), and an appropriate amount of water as a diluent. 1.0 mL of each solution was applied to three replicates of filter paper, 90 millimeters in diameter, contained in petri dishes (Treated Groups). Treated Groups and three replicates of an untreated Control Group were allowed to dry for two hours prior to infestation with a known number of adult bed bugs (approximately half male and half female).

Bed bug mortality was assessed immediately after infestation and at 2-, 4-, 8-, 12-, and 24-hour intervals after infestation, and daily thereafter until 33 days after infestation. Adult bed bugs were counted dead if they were unresponsive when stimulated. Table 4 summarizes the $LT_{50}$ (the mean point of time at which 50% of bed bugs had died), the 95% Confidence Interval (C.I.) and the maximum mortality observed for each formulation.

TABLE 4

$LT_{50}$ and Maximum Mortality of Formulations Incorporating Pesticidal Natural Oils.

| Pesticidal Natural Oil | Solvent | $LT_{50}$ (hrs.) | 95% C.I. (hrs.) | Max mortality |
|---|---|---|---|---|
| Cinnamon Oil | Acetophenone | 3.06 | 2.77 to 3.36 | 100% |
| Cinnamon Oil | Ethyl Lactate | 14.00 | 13.16 to 15.05 | 100% |
| Clove Oil | Acetophenone | 5.25 | 4.90 to 5.59 | 100% |
| Clove Oil | Ethyl Lactate | 10.58 | 10.03 to 11.11 | 100% |
| Eugenol | Acetophenone | 2.82 | 2.62 to 3.02 | 100% |
| Eugenol | Ethyl Lactate | 9.91 | 9.73 to 10.12 | 100% |
| Oregano Oil | Acetophenone | 2.00 | Interrupted** | 100% |
| Oregano Oil | Ethyl Lactate | 9.53 | 9.32 to 9.74 | 100% |
| Thyme Oil | Acetophenone | 3.10 | 2.89 to 3.31 | 100% |
| Thyme Oil | Ethyl Lactate | 17.24 | 16.65 to 17.82 | 100% |
| Garlic Oil | Acetophenone | 11.98 | 10.86 to 13.09 | 90% |
| Garlic Oil | Ethyl Lactate | 24.54 | 7.27 to 41.80 | 100% |
| Anise Oil | Acetophenone | 17.79 | 16.56 to 19.01 | 100% |
| Anise Oil | Ethyl Lactate | 227.8 | N/A* | 30% |
| Geranium Oil | Acetophenone | 2.00 | Interrupted** | 100% |
| Geranium Oil | Ethyl Lactate | 16.93 | N/A* | 90% |
| Lime Oil | Acetophenone | 6.628 | N/A* | 89% |
| Lime Oil | Ethyl Lactate | 93.35 | N/A* | 45% |
| Peppermint Oil | Acetophenone | 2.18 | 2.15 to 2.22 | 100% |
| Peppermint Oil | Ethyl Lactate | N/A* | N/A* | 55% |
| Lavender Oil | Acetophenone | 3.57 | 3.01 to 4.14 | 100% |
| Lavender Oil | Ethyl Lactate | N/A* | N/A* | 40% |
| Neem Oil | Acetophenone | 6.54 | 6.07 to 7.02 | 100% |
| Neem Oil | Ethyl Lactate | N/A* | N/A* | 40% |
| Control | None | N/A* | N/A* | 30% |

*N/A: $LT_{50}$ and 95% C.I. cannot be reliably calculated for formulations that do not reach 100% maximum mortality

**Interrupted: 95% C.I. cannot be reliably calculated when the $LT_{50}$ is below two hours Example 3—Dry Residual Insecticidal Activity of Various Solvents This example illustrates the dry residual pesticidal activity of formulations including neem oil and various organic solvents including alcohols, ketones, esters and carboxylic acids. Solutions were prepared using 5.5% by weight neem oil; the percent by weight of organic solvent indicated in Table 5 and an appropriate amount of isopropanol as a carrier diluent. The percent by weight of each solvent was varied to ensure a consistent molar quantity of solvent in each solution (final concentration of 1.5 mol/kg). Treated Groups for each solution were prepared by treating filter paper, 90 mm in diameter, with 1.0 mL of solution and allowing it to air dry for four hours. A known number of adults were added to each treated dish, four hours after treatment. Bed bug mortality was assessed immediately after infestation and at 1-hour, 2-hour, 4-hour, 6-hour, 8-hour, 10-hour, 12-hour, and 24-hour intervals, and at 24-hour intervals thereafter until 14 days after infestation. Adult bed bugs were counted dead if they were unresponsive when stimulated. Table 5 shows the maximum % mortality of all treated groups and the time taken to reach maximum mortality.

A number of the tested organic solvents, from the classes of alcohols, ketones, esters and carboxylic acids, proved effective in combination with neem oil. Solvents that included at least one aryl group were generally more effective than solvents that contained only alkyl groups. Alkyl aryl ketones were consistently effective solvents, and small aryl alcohols, aryl alkyl alcohols, aryl aryl ketones, and alkyl aryl esters also proved effective in combination with neem oil.

TABLE 5

Maximum % Mortality of Formulations with Differing Organic Solvents.

| Class of Solvent | Formula | % Solvent (w/w) | Compound name | Max. Mortality | Time to Max Mortality |
|---|---|---|---|---|---|
| *Alcohol X = CH(OH)* | | | | | |
| Alkyl alcohols | Alk—X—H | | | | |
| | Alk = butyl | 11.26 | 1-Butanol | 40% | 8 d |
| | Alk = hexyl | 15.52 | 1-Hexanol | 40% | 14 d |
| | Alk = ethyl-pentyl (Branched alkyl) | 19.78 | 2-Ethyl-1-hexanol | 100% | 72 hr |
| | Alk = decyl | 24.04 | 1-Decanol | 100% | 11 d |
| Isoalcohols | Alk$_1$—X—Alk$_2$ | | | | |
| | Alk$_1$ = methyl, Alk$_2$ = methyl | 93.25 | 2-Propanol (IPA) | 40% | 6 d |
| | Alk$_1$ = ethyl, Alk$_2$ = methyl | 11.26 | 2-Butanol | 20% | 14 d |
| | Cyclohexanol | 15.21 | Cyclohexanol | 60% | 14 d |
| Aryl alcohol | Ar—X—H | | | | |
| | Ar = phenyl | 16.42 | Benzyl alcohol | 100% | 24 hr |
| Aryl-alkyl alcohol | Ar—X—Alk | | | | |
| | Ar = phenyl, Alk = methyl | 18.56 | 1-Phenylethanol | 100% | 24 hr |
| *Aldehyde and Ketone X = (C=O)* | | | | | |
| Aldehyde | Ar—X—H | | | | |
| | Ar = phenyl | 16.12 | Benzaldehyde | 100% | 14 d |
| Alkyl-Alkyl ketone | Alk$_1$—X—Alk$_2$ | | | | |
| | Alk$_1$ = methyl, Alk$_2$ = cyclohexyl | 19.17 | Methylcyclohexylketone | 70% | 11 d |
| | Cyclohexanone | 14.91 | Cyclohexanone | 50% | 10 d |
| Aryl-Alkyl ketone | Ar—X—Alk | | | | |
| | Ar = phenyl, Alk = methyl | 18.25 | Acetophenone | 100% | 24 hr |
| | Ar = 4-methylphenyl, Alk = methyl | 20.38 | 4'-Methylacetophenone | 100% | 48 hr |
| | Ar = 2,4-dimethylphenyl, Alk = methyl | 22.51 | 2',4'-Dimethylacetophenone | 100% | 24 hr |
| | Ar = 3,4-dimethylphenyl, Alk = methyl | 22.51 | 3',4'-Dimethylacetophenone | 100% | 48 hr |
| | Ar = phenyl, Alk = ethyl | 20.69 | Propiophenone | 100% | 24 hr |
| | Ar = 4-methylphenyl, Alk = ethyl | 22.51 | 4'-Methylpropiophenone | 100% | 24 hr |
| | Ar = phenyl, Alk = propyl | 22.51 | Butyrophenone | 100% | 24 hr |
| | Ar = phenyl, Alk = isopropyl | 22.51 | Isobutyrophenone | 100% | 48 hr |
| | Ar = phenyl, Alk = butyl | 24.64 | Valerophenone | 100% | 24 hr |
| | Ar = phenyl, Alk = pentyl | 26.77 | Hexanophenone | 100% | 6 d |
| Aryl-aryl ketone | Ar$_1$—X—Ar$_2$ | | | | |
| | Ar$_1$ = 2,4-dihydroxyphenyl, Ar$_2$ = 2,4-dihydroxyphenyl | 37.4 | 2,2'-4,4' Tetrahydroxybenzophenone | 100% | 24 hr |
| *Carboxylic Acids and Esters X = (C=O)—O* | | | | | |
| Alkyl-alkyl ester | Alk$_1$—X—Alk$_2$ | | | | |
| | Alk$_1$ = methyl, Alk$_2$ = ethyl | 13.38 | Ethyl acetate | 30% | 14 d |
| | Alk$_1$ = methyl, Alk$_2$ = 2-tert-butylcyclohexyl | 30.12 | 2-tert-Butylcyclohexylacetate | 100% | 96 hr |
| Aryl acid | Ar—X—H | | | | |
| | Ar = phenyl | 18.55 | Benzoic acid | 100% | 48 hr |
| Aryl-alkyl ester | Ar—X—Alk | | | | |
| | Ar = 4-hydroxyphenyl, Alk = propyl | 27.27 | Propyl-4-hydroxybenzoate | 100% | 24 hr |

Example 4—Dry Residual Insecticidal Activity of Various Solvents

This example illustrates the dry residual pesticidal activity of formulations including neem oil and various organic solvents including alcohols, ketones, esters and carboxylic acids. Solutions were prepared using 5.5% by weight neem oil; 1.5 mol/kg organic solvent; and an appropriate amount of isopropanol as a carrier diluent. The percent by weight of each solvent was varied to ensure a consistent molar quantity of solvent in each solution. Treated Groups for each solution were prepared by treating filter paper, 90 mm in diameter, with 1.0 mL of solution and allowing it to air dry for four hours in a highly-ventilated room. A known number of adults were added to each treated dish, four hours after treatment. Bed bug mortality was assessed immediately after infestation and at 1-hour, 2-hour, 4-hour, 6-hour, 8-hour, 10-hour, 12-hour, and 24-hour intervals, and at 24-hour intervals thereafter until 14 days after infestation. Adult bed bugs were counted dead if they were unresponsive when stimulated. Table 6 shows the maximum % mortality of all treated groups and the time taken to reach maximum mortality.

A number of the tested organic solvents, from the classes of alcohols, ketones, esters, ethers, aldehydes and carboxylic acids, proved effective in combination with neem oil. Solvents that included at least one aryl group were generally more effective than solvents that contained only alkyl groups.

TABLE 6

Maximum % Mortality of Formulations with Differing Organic Solvents.

| Class | Formula and ID | Compound name | Max. Mortality | Time to Max Mortality |
|---|---|---|---|---|
| | | Alcohol X = CH(OH) | | |
| Alkyl alcohol | Alk—X—H | | | |
| | Alk = nonyl | 1-Nonanol | 100% | 48 hr |
| | Alk = butyl-heptyl (Branched alkyl) | 2-Butyl-1-octanol | 100% | 8 d |
| | Alk = dodecyl | 1-dodecanol | 90% | 14 d |
| | Alk = hexyl-nonyl (Branched alkyl) | 2-hexyl-1-decanol | 100% | 14 d |
| Isoalcohol | $Alk_1$—X—$Alk_2$ | | | |
| | $Alk_1$ = butyl $Alk_2$ = ethyl | 3-Heptanol | 30% | 14 d |
| | $Alk_1$ = hexyl $Alk_2$ = methyl | 2-Octanol | 100% | 48 hr |
| | $Alk_1$ = isobutyl $Alk_2$ = isobutyl | 2,6-Dimethyl-4-heptanol | 20% | 14 d |
| Aryl alcohol | Ar—X—H | | | |
| | Ar = 3,4-dimethylphenyl | 3,4-dimethylbenzyl alcohol | 100% | 14 d |
| Aryl-alkyl alcohol | Ar—X—Alk | | | |
| | Ar = 4-methylphenyl Alk = methyl | Alpha-4-dimethylbenzyl alcohol | 100% | 24 hr |
| | Ar = phenyl Alk = dimethyl | 2-Phenyl-2-propanol | 100% | 24 hr |
| | | Aldehyde and Ketone X = (C=O) | | |
| Aryl-Aldehyde | Ar—X—H | | | |
| | Ar = 4-methylphenyl | p-Tolualdehyde | 50% | 6 d |
| | Ar = 2-hydroxy-5-methylphenyl | 2-hydroxy-5-methyl benzaldehyde | 100% | 24 hr |
| Aryl-Alkyl ketone | Ar—X—Alk | | | |
| | Ar = 4-hydroxyphenyl Alk = methyl | 4'-Hydroxyacetophenone | 50% | 9 d |
| | Ar = 2-hydroxyphenyl Alk = methyl | 2'-Hydroxyacetophenone | 100% | 24 hr |
| | Ar = 4-hydroxyphenyl Alk = butyl | 4'-Hydroxyvalerophenone | 70% | 14 d |
| | Ar-phenyl Alk = cyclohexyl | Cyclohexyl phenyl ketone | 90% | 8 d |
| | | Carboxylic Acids and Esters X = (C=O)—O | | |
| Aryl acid | Ar—X—H | | | |
| | Ar = 4-hydroxyphenyl | 4-Hydroxy benzoic acid | 100% | 24 hr |
| | Ar = 4-hydroxy-3-methylphenyl | 4-Hydroxy-3-methyl benzoic acid | 60% | 14 d |
| Aryl-alkyl ester | Ar—X—Alk | | | |
| | Ar = phenyl Alk = ethyl | Ethyl benzoate | 100% | 48 hr |
| | Ar = phenyl Alk = isobutyl | Isobutyl benzoate | 90% | 8 d |
| Aryl-aryl ester | Ar—X—Ar | | | |
| | Ar = phenyl Alk = benzyl | Benzyl benzoate | 100% | 8 d |

TABLE 6-continued

Maximum % Mortality of Formulations with Differing Organic Solvents.

| Class | Formula and ID | Compound name | Max. Mortality | Time to Max Mortality |
|---|---|---|---|---|
| Phenol and Ethers X = O | | | | |
| Aryl-Alkyl ether | Ar—X—H | Phenol | 100% | 24 hr |
| | Ar—X—Alk | | | |
| | Ar = benzyl Alk = methyl | Benzyl methyl ether | 60% | 8 d |
| | Ar = phenyl Alk = butyl | Butyl phenyl ether | 100% | 6 d |
| | Ar = 4-(1-propenyl)benzyl Alk = methyl | Trans-anethole | 100% | 5 d * |
| Aryl-Aryl ether | Ar—X—Ar | | | |
| | $Ar_1$ = benzyl $Ar_2$ = benzyl | Dibenzyl ether | 90% | 7 d |
| | $Ar_1$ = phenyl $Ar_2$ = phenyl | Diphenyl ether | 100% | 72 hr |
| Benzenes | | | | |
| | | Benzene | 40% | 14 d |
| | | Toluene | 50% | 14 d |
| | | p-Xylene | 30% | 14 d |

* Solvent tested in separate study from other solvents in table (under same experimental conditions)

Example 5—Dry Residual Insecticidal Activity

Three solutions were prepared, each containing isopropanol as a carrier diluent: 'Solution A' included 5.5% neem oil and 1.25% castor oil by weight; 'Solution B' included 18.25% acetophenone and 1.25% castor oil by weight; and 'Solution C' included 5.5% neem oil, 18.25% acetophenone, and 1.25% castor oil by weight. 1.0 mL of each solution was applied to one replicate of filter paper, 90 millimeters in diameter, contained in petri dishes (Treated Groups). An untreated Control Group was tested concurrently. All Treated Groups were allowed to dry for four hours prior to infestation with adult bed bugs.

Bed bug mortality was assessed immediately after infestation and at 2-, 4-, 8-, 10-, and 24-hour intervals after infestation. Adult bed bugs were counted dead if they were unresponsive when stimulated. Table 7 summarizes the mean mortality data of all formulations at the stated observation intervals.

Solution C demonstrated significantly higher pesticidal activity at all observed intervals, than a solution of acetophenone alone (Solution B) or neem oil alone (Solution A).

TABLE 7

Mean % Mortality of 4-Hour Dry Residues.

| | | 0 HR | 2 HR | 4 HR | 8 HR | 10 HR | 24 HR |
|---|---|---|---|---|---|---|---|
| Control | No Treatment | 0% | 0% | 0% | 0% | 0% | 0% |
| Solution A | 5.5% Neem Oil | 0% | 0% | 0% | 0% | 0% | 9% |
| Solution B | 18.25% Acetophenone | 0% | 0% | 0% | 0% | 10% | 70% |
| Solution C | 5.5% Neem Oil + 18.25% Acetophenone | 0% | 30% | 40% | 60% | 70% | 90% |

Example 6—Dry Residual Insecticidal Activity

Six solutions were prepared, each containing isopropanol as a carrier diluent: 'Solution A' included 5.5% neem oil by weight, 15.5% acetophenone by weight, 1.8% natural oils (lemongrass oil and wintergreen oil) by weight and 1.25% surfactant by weight; 'Solution B' included 5.5% neem oil by weight, 15.5% acetophenone by weight, and 5.0% surfactant by weight; 'Solution C' included 5.5% neem oil alone by weight; 'Solution D' included 15.5% acetophenone alone by weight; 'Solution E' included 1.8% natural oils (lemongrass oil and wintergreen oil) by weight; and 'Solution F' included 5.5% neem oil by weight and 15.5% acetophenone by weight. 1.0 mL of each solution was applied to filter paper, 90 millimeters in diameter, contained in petri dishes (the Treated Groups). The surfactant used in all solutions was ethoxylated castor oil. Two replicates for each Treated Group and two replicates of a negative Control Group were tested concurrently. Treated surfaces were sealed in petri dishes with a plastic paraffin film and allowed to sit for eight days, then were exposed to the air for four hours, prior to infestation with a known number of adult bed bugs.

Immediately after infestation and at 4-, 8-, 12-, 24-, 48-, 72-, 96-, 120-, and 144-hour intervals after infestation, the number of bed bugs killed in the intervening period was assessed. Adult bed bugs were counted dead if they were unresponsive when stimulated. The mean percentage of dead adult bed bugs was calculated for each interval and compared for efficacy to the data from all other formulations. Table 8 summarizes the mean mortality data of all formulations at the stated observation intervals.

Solutions A, B and F demonstrated a similar level of activity, and all demonstrated markedly improved dry residue pesticidal activity relative to both neem oil alone (Solution C), acetophenone alone (Solution D), and essential oils alone (Solution E), particularly at earlier time points between 12 hours and 120 hours.

TABLE 8

Mean % Mortality of 8-Day Old Residues.

|  | 0 HR | 4 HR | 8 HR | 12 HR | 24 HR | 48 HR | 72 HR | 96 HR | 120 HR | 144 HR |
|---|---|---|---|---|---|---|---|---|---|---|
| Control | 0.0% | 0.0% | 0.0% | 0.0% | 0.0% | 0.0% | 0.0% | 0.0% | 0.0% | 0.0% |
| Solution A | 0.0% | 0.0% | 10.0% | 40.0% | 65.0% | 75.0% | 90.0% | 95.0% | 95.0% | 100.0% |
| Solution B | 0.0% | 0.0% | 10.0% | 25.0% | 55.0% | 80.0% | 90.0% | 90.0% | 90.0% | 90.0% |
| Solution C | 0.0% | 0.0% | 0.0% | 0.0% | 0.0% | 5.0% | 5.0% | 5.0% | 5.0% | 5.0% |
| Solution D | 0.0% | 0.0% | 5.0% | 5.0% | 10.0% | 25.0% | 45.0% | 45.0% | 65.0% | 80.0% |
| Solution E | 0.0% | 0.0% | 0.0% | 0.0% | 0.0% | 10.0% | 10.0% | 25.0% | 30.0% | 30.0% |
| Solution F | 0.0% | 10.0% | 20.0% | 35.0% | 65.0% | 75.0% | 90.0% | 100.0% | 100.0% | 100.0% |

Example 7—Prolonged Residual Pesticidal Activity

This example illustrates the prolonged residual pesticidal activity of combinations of neem oil, acetophenone, and a surfactant against bed bugs. The method used in this example facilitates assessment of the necessary retreatment interval for a pesticidal composition. A solution comprising 5.5% neem oil by weight, 15.5% acetophenone by weight, 8% natural oils (lemongrass oil, spearmint oil, clove oil, and wintergreen oil) by weight and 5.0% ethoxylated castor oil by weight was prepared and combined with an appropriate amount of isopropyl alcohol as a carrier diluent. 1.0 mL of each solution was applied to unpainted plywood surfaces, 90 millimeters in diameter, contained in petri dishes. Five replicates were done as a Treated Group, and five replicates were done for an untreated negative Control Group tested concurrently. All Treated Group substrates were treated at the beginning of the experiment, then allowed to air dry until the time of infestation. On Day 1, adult bed bugs were infested either immediately after treatment, or two hours after treatment (when the substrate was dry). On following days until Day 30, adult bed bugs were infested onto replicates of substrates treated on Day 1 and air-dried since. At intervals after infestation of bed bugs each day, the number of bed bugs killed in the intervening period was counted. Adult bed bugs were counted dead if unresponsive when stimulated.

The percentage of dead adult bed bugs was calculated for each daily interval and compared for efficacy to the data from the Control Group. Table 9 presents the mean mortality data for the Treated and Control Groups for up to 27 days after the Day 1 treatment, at the 15-day observation interval. While the Controls in this experiment exhibited higher than normal mortality (perhaps because of contamination of treated substrates or due to glue epoxy used to seal the substrates within petri dishes) the Treated Groups nonetheless exhibited significantly improved pesticidal activity when compared with the Control Groups for treatments up to 27 days old.

TABLE 9

Mean % Mortality of Compositions after Prolonged Dry Times, Observed 15 Days after Infestation

| Days After Treatment, Prior to Infestation | | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| % Mortality | Treated Group | 100 | 100 | 100 | 100 | 100 | 100 | 100 | 100 | 100 | 100 | 100 | 83 | 97 | 87 |
| | Control Group | 40 | 57 | 40 | 13 | 23 | 43 | 0 | 23 | 7 | 10 | 30 | 37 | 10 | 0 |
| Days After Treatment, Prior to Infestation | | 15 | 16 | 17 | 18 | 19 | 20 | 21 | 22 | 23 | 24 | 25 | 26 | 27 | |
| % Mortality | Treated Group | 100 | 97 | 100 | 100 | 90 | 87 | 90 | 77 | N/A* | 70 | 90 | 53 | 60 | |
| | Control Group | 19 | 36 | 17 | 32 | 33 | 43 | 50 | 13 | 10 | 24 | 12 | 6 | 37 | |

*N/A = data not available

Example 8—Prevention of Bed Bug Egg Emergence

This example illustrates the prevention of egg emergence by a composition including neem oil, acetophenone, and an appropriate surfactant. The dry residue prevention of bed bug egg emergence is compared among different methods of applying the composition and to an untreated control group. A solution comprising 5.5% neem oil by weight, 15.5% acetophenone by weight, 8% natural oils (lemongrass oil, spearmint oil, clove oil, and wintergreen oil) by weight and 5.0% ethoxylated castor oil by weight was prepared and combined with an appropriate amount of isopropyl alcohol as a carrier diluent. Three different Treated Groups were prepared, one of filter paper treated with 1.0 mL of solution and allowed to air dry prior to introduction of eggs, one of filter paper with eggs laid on it treated with 1.0 mL of solution added to the edge of the substrate and allowed to wick underneath the eggs, and one where eggs were sprayed directly. Five replicates for each Treated Group, and five negative Control Group were tested concurrently.

At daily intervals, the numbers of hatched and unhatched eggs present in the sealed dishes were counted and compared to other Treated Groups and the Control Group. One egg was counted as "hatched" for every new nymph present in the petri dish when compared with the prior interval.

While the eggs in the Control Group hatched at the predicted interval of approximately 7 days, none of the eggs in any of the Treated Groups had hatched by experiment's end 16 days post-treatment. No difference was observed between spray treatments, wet treatments, and dry residue treatments. FIG. 1 shows the egg emergence data of the treated groups at the stated daily intervals (the three treated groups having identical data sets) as compared to the Untreated Control.

Table 10 summarizes the prolonged dry residual egg emergence data from a similar study of the same formulation as described above, over a longer period of time. 1.0 mL of the composition was dried for two hours prior to introduction of bed bug eggs, and completely prevented egg eclosion up to 19 days after its application to a filter paper substrate.

tellidae (although some commentators consider cockroaches to belong to the order Orthoptera), than bed bugs, which belong to the order Hemiptera. Both cockroaches and bed bugs reproduce relatively quickly compared to other arthropods. Without being bound by theory, this rapid reproduction may contribute to the ability of these pests to survive insecticide treatments. Preventing egg emergence of bed bugs, cockroaches and other arthropods can therefore potentially assist in eliminating these pests.

Example 10—Prevention of Oviposition and Egg Emergence in Bed Bugs

This example illustrates the prevention of egg emergence of a combination of neem oil and acetophenone, as compared with neem oil alone.

A concentrated solution, 'Solution B,' including 25% neem oil by weight, 70% acetophenone by weight, and 5.0%

TABLE 10

Mean % Bed Bug Egg Eclosion Observed 15 days after Infestation.

| Days After Treatment | | 1 | 2 | 3 | 4 | 5 | 6 | 7 | 8 | 9 | 10 | 11 | 12 | 13 |
|---|---|---|---|---|---|---|---|---|---|---|---|---|---|---|
| % Eclosion | Treated Group | 0 | 0 | 0 | 0 | 0 | 0 | 0 | 0 | 0 | 2 | 0 | 0 | 0 |
| | Control Group | 59 | 56 | 39 | 49 | 51 | 33 | 55 | 53 | 66 | 81 | 72 | 70 | 67 |
| Days After Treatment | | 14 | 15 | 16 | 17 | 18 | 19 | 20 | 21 | 22 | 23 | 24 | 25 | |
| % Eclosion | Treated Group | 0 | 0 | 0 | 0 | 0 | 0 | 7 | 27 | 33 | N/A* | 100 | 100 | |
| | Control Group | 100 | 100 | 99 | 100 | 100 | 100 | 100 | 100 | 97 | 100 | 100 | 100 | |

*N/A = data not available

Example 9—Prevention of Cockroach Egg Emergence

The dry residue prevention of cockroach egg emergence was compared by exposing cockroach eggs (grouped as oothecae) to the composition and to an untreated control substrate. A solution comprising 22% neem oil by weight, 73% acetophenone by weight and 5.0% ethoxylated castor oil by weight was prepared and applied to filter paper at a rate of 800 ft$^2$/gal of solution. Following air-drying, treated paper was sealed inside plastic tubes (10 cm×3 cm diam.) along with gravid female cockroaches containing eggs. Female cockroaches and eggs were exposed to such treated or control (untreated) papers for 15 days after initial treatment. Ten replicates for each Treated Group, and ten negative Control Group were tested concurrently.

At daily intervals, the numbers of hatched and unhatched eggs present in the sealed tubes were counted and compared to the Control Group. One egg from each ootheca was counted as "hatched" for every new nymph present in the tube when compared with the prior interval.

Figure 2:
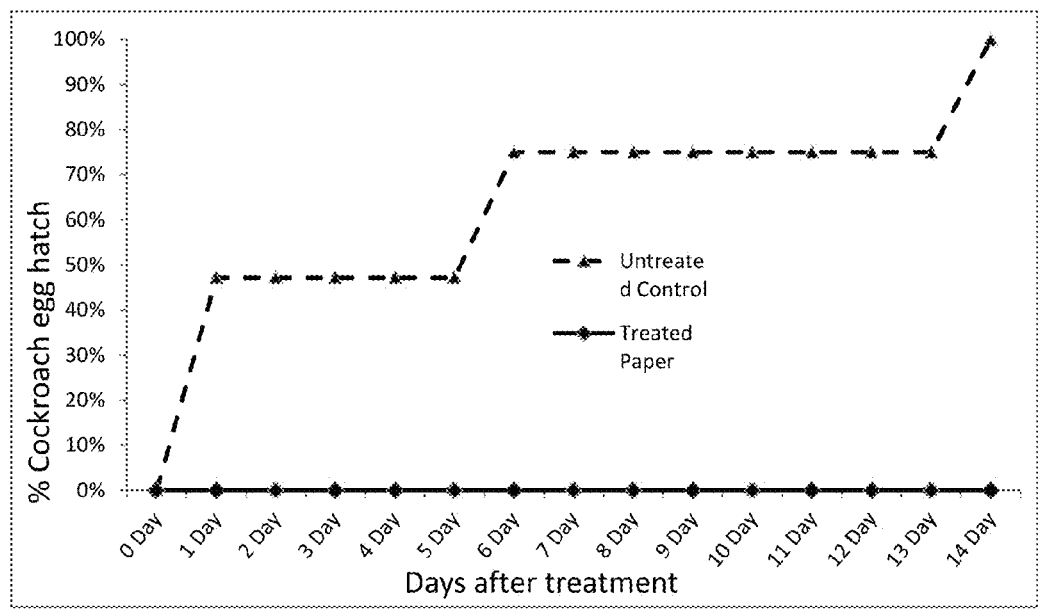
FIG. 2 shows the results of an example testing the prevention of cockroach egg emergence by a composition according to one example embodiment.

While the eggs in the Control Group hatched at the predicted interval of 1-14 days, none of the eggs in the Treated Group had hatched by experiment's end, 14 days post-treatment. FIG. 2 shows the egg emergence data of the treated group at the stated daily intervals as compared to the Untreated Control.

Both cockroaches and bed bugs are arthropods. Cockroaches belong to a more primitive taxonomic order, Blatethoxylated castor oil by weight was prepared. Dilutions of this concentrated solution were prepared, each containing ethanol as the carrier diluent. Dilutions containing 15% of Solution B (final concentration of 3.75% neem oil and 10.5% acetophenone by weight)—or greater—killed 100% of adults infested on the treated surface and no eggs were laid. Dilutions of 10% or less of Solution B were insufficient to kill adult bed bugs before eggs were laid on the treated substrates in these groups; these dilutions were monitored for oviposition and eclosion, and are compared to positive control treatments of neem oil alone (10% solution in diluent) and negative controls treated only with the carrier diluent. 'Formulation A' included 10% neem oil by weight diluted in ethanol, 'Formulation B' contained 10% by volume of the concentrated Solution B described above diluted in ethanol (final concentration of 2.5% neem oil and 7% acetophenone by weight); 'Formulation C' included 1% by volume of the concentrated Solution B (final concentration of 0.25% neem oil and 0.7% acetophenone by weight); and 'Formulation D' included 0.1% by volume of the concentrated Solution B (final concentration of 0.025% neem oil and 0.07% acetophenone by weight).

Table 11 summarizes egg emergence and oviposition observations for the tested compositions and controls. Oviposition was seen on 10-day-old dry treatments of all the above solutions and controls, but was significantly reduced on the sample treated with a 10% dilution of Solution B (Formulation B). Eclosion was observed on both negative controls and Formulation A (neem oil only) treatments, and on dilutions of the concentrated Solution B of 0.1% (Formulation D) and lower concentrations. No egg emergence was exhibited on dilutions of 1.0% of the concentrated Solution B or more (Formulation B and C).

TABLE 11

Eclosion and Oviposition Observations of a Serial Dilution of an Exemplary Composition, Compared with Control and Neem Oil Alone, Observed 10-13 Days after Infestation.

|  | 10 Day | | 11 Day | | 12 Day | | 13 Day | |
| --- | --- | --- | --- | --- | --- | --- | --- | --- |
|  | # eggs | # emerged | # eggs | # emerged | # eggs | # emerged | # eggs | # emerged |
| Negative Control | 29 | 0 | 31 | 0 | 31 | 11 | 31 | 11 |
| Formulation A (10% Neem Oil) | 22 | 0 | 23 | 0 | 25 | 8 | 25 | 8 |
| Formulation B (2.5% Neem Oil + 7% Acetophenone) | 4 | 0 | 4 | 0 | 4 | 0 | 4 | 0 |
| Formulation C (0.25% Neem Oil + 0.7% Acetophenone) | 18 | 0 | 19 | 0 | 18 | 0 | 18 | 0 |
| Formulation D (0.025% Neem Oil + 0.07%Acetophenone) | 35 | 0 | 36 | 0 | 34 | 9 | 34 | 9 |

Example 11—Prevention of Egg Emergence by Various Pesticidal Natural Oils

This example illustrates the prevention of egg emergence of formulations including a natural oil and acetophenone. Solutions were prepared according to Table 12 below, comprising 2.5% by weight active oil ingredient, 5.0% by weight solvent (either ethyl lactate or acetophenone), and an appropriate amount of water as a carrier diluent. Treated Groups for each solution were prepared by treating filter paper, 90 mm in diameter, with 1.0 mL of solution and allowed to air dry for two hours. Five bed bug eggs were added to each treated dish, two hours after treatment. Immediately after infestation, and at 1-, 2-, and 3-week intervals thereafter, the numbers of hatched and unhatched eggs present in the sealed dishes were counted and compared to other Treated Groups. One egg was counted as "hatched" for every new nymph present in the petri dish when compared with the prior interval. Table 12 compares the mean % egg eclosion of the treated groups at three weeks post-infestation. The maximum mortality data obtained in Example 2, above, are included for each formulation, for comparison purposes.

All dishes treated with 2.5% by weight natural oils and 5.0% by weight ethyl lactate exhibited some eclosion at all weekly observation intervals (up to 80% eclosion for combinations of ethyl lactate with clove oil, thyme oil, garlic oil, lavender oil, and lime oil). Combinations of 2.5% by weight cinnamon oil, thyme oil, garlic oil, anise oil, geraniol, and geranium oil with 5.0% acetophenone by weight resulted in complete prevention of egg eclosion across all observation intervals. Combinations of 2.5% by weight clove oil, eugenol, and oregano oil exhibited some increased prevention of egg emergence relative to solutions of ethyl lactate, although some egg emergence was observed. Solutions with 2.5% clove oil, eugenol, and oregano oil all exhibited complete prevention of egg eclosion when combined with 15.5% acetophenone by weight. Among those tested, the natural oils that exhibited stronger insecticidal activity on adult bed bugs also generally exhibited stronger ovicidal activity and prevention of egg emergence.

TABLE 12

Mean % Eclosion of Formulations Incorporating Various Natural Oils.

| Pesticidal Natural Oil | Solvent | Max mortality | % Eclosion (3 weeks post-infest.) |
| --- | --- | --- | --- |
| Cinnamon Oil | Acetophenone | 100% | 0% |
| Cinnamon Oil | Ethyl Lactate | 100% | 40% |
| Clove Oil | Acetophenone | 100% | 20% |
| Clove Oil | Ethyl Lactate | 100% | 80% |
| Eugenol | Acetophenone | 100% | 20% |
| Eugenol | Ethyl Lactate | 100% | 40% |
| Oregano Oil | Acetophenone | 100% | 20% |
| Oregano Oil | Ethyl Lactate | 100% | 40% |
| Thyme Oil | Acetophenone | 100% | 0% |
| Thyme Oil | Ethyl Lactate | 100% | 80% |
| Garlic Oil | Acetophenone | 90% | 0% |
| Garlic Oil | Ethyl Lactate | 100% | 80% |
| Anise Oil | Acetophenone | 100% | 0% |
| Anise Oil | Ethyl Lactate | 30% | 40% |
| Geranium Oil | Acetophenone | 100% | 0% |
| Geranium Oil | Ethyl Lactate | 90% | 60% |
| Lime Oil | Acetophenone | 89% | 0% |
| Lime Oil | Ethyl Lactate | 45% | 80% |
| Peppermint Oil | Acetophenone | 100% | 0% |
| Peppermint Oil | Ethyl Lactate | 55% | 60% |
| Lavender Oil | Acetophenone | 100% | 0% |
| Lavender Oil | Ethyl Lactate | 40% | 80% |
| Neem Oil | Acetophenone | 100% | N/A** |
| Neem Oil | Ethyl Lactate | 40% | N/A** |
| Control | None | 30% | 100% |

**N/A: Test not performed

Example 12—Prevention of Egg Emergence with Various Solvents

This example illustrates the dry residual pesticidal activity of formulations including neem oil and various organic solvents including alcohols, ketones, esters and carboxylic acids. Solutions were prepared using 5.5% by weight neem oil; the percent by weight of organic solvent indicated in Table 13 and an appropriate amount of isopropanol as a carrier diluent. Treated Groups for each solution were prepared by treating filter paper, 90 mm in diameter, with 1.0 mL of solution and allowing it to air dry for four hours. Five eggs were added to each treated dish, four hours after treatment. Immediately after infestation, and at 1-, 2-, and 3-week intervals thereafter, the numbers of hatched and unhatched eggs present in the sealed dishes were counted and compared to other Treated Groups. One egg was counted as "hatched" for every new nymph present in the petri dish when compared with the prior interval. Table 13 compares the % egg eclosion of the treated groups at the 3-week observation interval. The maximum mortality data obtained in Example 3, above, are included for comparison purposes.

A number of the tested organic solvents, from the classes of alcohols, ketones, esters and carboxylic acids, proved effective at preventing egg eclosion in combination with neem oil. Solvents that included at least one aryl group were generally more effective at preventing egg emergence than solvents that contained only alkyl groups. Alkyl aryl ketones were consistently effective solvents, and small aryl alcohols, aryl alkyl alcohols, aryl aryl ketones, and alkyl aryl esters also proved effective at preventing emergence in combination with neem oil. Among those tested, the organic solvents that exhibited stronger insecticidal activity on adult bed bugs generally also exhibited stronger ovicidal activity and prevention of egg emergence.

TABLE 13

% Bed Bug Egg Eclosion Observed 3 Weeks after Infestation.

| Class of Solvent | Formula | % Solvent (w/w) | Compound name | Max. Mortality | % Eclosion |
|---|---|---|---|---|---|
| Alcohol X = CH(OH) | | | | | |
| Alkyl alcohols | Alk—X—H | | | | |
| | Alk = butyl | 11.26 | 1-Butanol | 40% | 100% |
| | Alk = hexyl | 15.52 | 1-Hexanol | 40% | 0% |
| | Alk = ethyl-pentyl (Branched alkyl) | 19.78 | 2-Ethyl-1-hexanol | 100% | 0% |
| | Alk = decyl | 24.04 | 1-Decanol | 100% | 0% |
| Isoalcohols | $Alk_1$—X—$Alk_2$ | | | | |
| | $Alk_1$ = ethyl $Alk_2$ = methyl | 11.26 | 2-Butanol | 20% | 100% |
| | Cyclohexanol | 15.21 | Cyclohexanol | 60% | 60% |
| Aryl alcohol | Ar—X—H | | | | |
| | Ar = phenyl | 16.42 | Benzyl alcohol | 100% | 0% |
| Aryl-alkyl alcohol | Ar—X—Alk | | | | |
| | Ar = phenyl Alk = methyl | 18.56 | 1-Phenylethanol | 100% | 0% |
| Aldehyde and Ketone X = (C=O) | | | | | |
| Aldehyde | Ar—X—H | | | | |
| | Ar = phenyl | 16.12 | Benzaldehyde | 100% | 0% |
| Alkyl-Alkyl ketone | $Alk_1$—X—$Alk_2$ | | | | |
| | $Alk_1$ = methyl $Alk_2$ = cyclohexyl | 19.17 | Methylcyclohexylketone | 70% | 80% |
| | Cyclohexanone | 14.91 | Cyclohexanone | 50% | 40% |
| Aryl-Alkyl ketone | Ar—X—Alk | | | | |
| | Ar = phenyl Alk = methyl | 18.25 | Acetophenone | 100% | 0% |
| | Ar = 4-methylphenyl Alk = methyl | 20.38 | 4'-Methylacetophenone | 100% | 0% |
| | Ar = 2,4-dimethylphenyl Alk = methyl | 22.51 | 2',4'-Dimethylacetophenone | 100% | 0% |
| | Ar = 3,4-dimethylphenyl Alk = methyl | 22.51 | 3',4'-Dimethylacetophenone | 100% | 0% |
| | Ar = phenyl Alk = ethyl | 20.69 | Propiophenone | 100% | 0% |
| | Ar = 4-methylphenyl Alk = ethyl | 22.51 | 4'-Methylpropiophenone | 100% | 0% |
| | Ar = phenyl Alk = propyl | 22.51 | Butyrophenone | 100% | 0% |
| | Ar = phenyl Alk = isopropyl | 22.51 | Isobutyrophenone | 100% | 0% |
| | Ar = phenyl Alk = butyl | 24.64 | Valerophenone | 100% | 0% |
| | Ar = phenyl Alk = pentyl | 26.77 | Hexanophenone | 100% | 0% |
| Aryl-aryl ketone | $Ar_1$—X—$Ar_2$ | | | | |
| | $Ar_1$ = 2,4-dihydroxyphenyl $Ar_2$ = 2,4-dihydroxyphenyl | 37.4 | 2,2'-4,4' Tetrahydroxybenzophenone | 100% | 0% |

TABLE 13-continued

% Bed Bug Egg Eclosion Observed 3 Weeks after Infestation.

| Class of Solvent | Formula | % Solvent (w/w) | Compound name | Max. Mortality | % Eclosion |
|---|---|---|---|---|---|
| Carboxylic Acids and Esters X = (C=O)—O | | | | | |
| Alkyl-alkyl ester | $Alk_1$—X—$Alk_2$ $Alk_1$ = methyl $Alk_2$ = ethyl | 13.38 | Ethyl acetate | 30% | 100% |
|  | $Alk_1$ = methyl $Alk_2$ = 2-tert-butylcyclohexyl | 30.12 | 2-tert-Butylcyclohexylacetate | 100% | 20% |
| Aryl acid | Ar—X—H Ar = phenyl | 18.55 | Benzoic acid | 100% | 0% |
| Aryl-alkyl ester | Ar—X—Alk Ar = 4-hydroxyphenyl Alk = propyl | 27.27 | Propyl-4-hydroxybenzoate | 100% | 0% |

Example 13—Insecticidal Knockdown Activity

This example illustrates the insecticidal knockdown activity of combinations of neem oil or derivatives thereof with acetophenone against bed bugs, when compared with knockdown activity of neem oil or derivative alone and acetophenone alone. Six solutions were prepared: 'Solution A' included 5.5% neem oil by weight, 1.25% ethoxylated castor oil by weight and 18.25% acetophenone by weight, and isopropanol as a carrier solvent; 'Solution B' included 5.5% neem oil by weight, 1.25% ethoxylated castor oil by weight, 18.25% acetophenone by weight, and water as a carrier solvent; 'Solution C' included 5.5% neem oil by weight, 1.25% ethoxylated castor oil by weight, and water as a carrier solvent; 'Solution D' included 18.25% acetophenone by weight, 1.25% ethoxylated castor oil by weight, and water as a carrier solvent; 'Solution F' included 0.3% azadirachtin A by weight, 1.25% ethoxylated castor oil by weight %, 18.25% acetophenone by weight, and water as a carrier solvent; and 'Solution F' included 0.3% azadirachtin A by weight, 1.25% ethoxylated castor oil by weight, and water as a carrier solvent. Adult bed bugs were infested on to petri dishes containing filter paper, 90 millimeters in diameter. Bed bugs were treated by applying 5 microliters of each solution to the ventral side. Mortality was assessed at intervals of 30 minutes, and 1-, 2-, 4-, 6-, 8-, 10-, 24-, 100-, and 342-hours after treatment. Bed bugs were counted dead if unresponsive when stimulated. The percentage of dead adult bed bugs was calculated and compared to data from all other formulations. Table 14 summarizes mortality data of respective formulations at the stated intervals.

The neem/acetophenone (Solutions A and B) and azadirachtin/acetophenone (Solution C) combinations performed better as knockdown killers than neem alone (Solution D), acetophenone alone (Solution E), and azadirachtin alone (Solution F).

TABLE 14

% Mortality of Neem Oil and Azadirachtin as Knockdown Killers of Adult Bed Bugs.

| % Mortality | Time (hours) | | | | | | | | | | |
|---|---|---|---|---|---|---|---|---|---|---|---|
|  | 0 | 0.5 | 1 | 2 | 4 | 6 | 8 | 10 | 24 | 100 | 342 |
| Solution A (5.5% neem oil, 18.25% acetophenone, 75% isopropanol) | 0 | 80 | 80 | 80 | 80 | 90 | 90 | 100 | 100 | 100 | 100 |
| Solution B (5.5% neem oil, 18.25% acetophenone, 75% water) | 0 | 60 | 60 | 60 | 60 | 70 | 80 | 80 | 90 | 80 | 100 |
| Solution C (0.3% azadirachtin A, 18.25% acetophenone, 80.2% water) | 0 | 30 | 30 | 30 | 30 | 40 | 70 | 80 | 100 | 100 | 100 |
| Solution D (5.5% neem oil, 93.25% water) | 0 | 30 | 40 | 40 | 50 | 50 | 50 | 50 | 50 | 60 | 50 |
| Solution E (18.25% acetophenone, 80.5% water) | 0 | 40 | 40 | 40 | 40 | 40 | 40 | 40 | 30 | 30 | 100 |
| Solution F (0.3% azadirachtin A, 98.45% water) | 0 | 0 | 0 | 0 | 0 | 0 | 0 | 0 | 0 | 0 | 10 |
| Water | 0 | 0 | 0 | 0 | 0 | 0 | 0 | 0 | 0 | 0 | 0 |
| Untreated Control | 0 | 0 | 0 | 0 | 0 | 0 | 0 | 0 | 0 | 0 | 0 |

Example 14—Broad Spectrum Pesticide Activity

This example illustrates the dry residue pesticidal activity of a combination of natural oil and solvent against arthropods (including insects) other than bed bugs. The tested arthropods were German cockroach (*Blattella germanica*), Smoky Brown cockroach (*Periplaneta fuliginosa*), American cockroach (*Periplaneta americana*), cellar spider (*Pholcus phalangiodes*) cat flea (*Ctenocephalides felis*), tick (Ixodidea family), fire ant (*Solenopsis Invicta*), termite (*Reticulitermes flavipes*), black carpenter ant (*Camponotus pennsylvanicus*), pavement ant (*Tetramorium caespitum*), field ant (*Formica* sp.), moisture ant (*Lasius* sp.), wood ant (*Formica rufa*), house fly (*Musca domestica*), bottle fly (*Lucilia sericata*), giant silverfish (*Ctenolepisma longicaudata*), firebrat (*Thermobia domestica*), bean aphid (*Aphis fabae*), and pea aphid (*Acyrthosiphon pisum*). A solution of 5.5% neem oil by weight, 15.5% acetophenone by weight, 2.65% natural oils (lemongrass oil, vanillin, and wintergreen oil) by weight and 1.25% ethoxylated castor oil by weight was combined with an appropriate amount of isopropyl alcohol as a carrier diluent. 1.0 mL of the solution was applied to filter paper surfaces, 90 millimeters in diameter, contained in petri dishes (the Treated Groups). Untreated Control replicates were tested concurrently. Treated substrates were allowed to air dry for two hours prior to infestation with a known number of adult arthropods. Dishes were infested according to the following schedule: three replicates of three adults apiece were prepared for American and Smoky Brown cockroaches; three replicates of five adults apiece were prepared for German cockroaches; nine replicates of one adult apiece were prepared for cellar spiders; and three replicates of 10 adults apiece were prepared for ticks, ants, termites, flies, aphids, silverfish, firebrats, and cat fleas. At 1-, 4-, and 24-hour intervals following the addition of arthropods, the number of arthropods killed in the intervening period was observed. The adult arthropods were counted dead if they were unresponsive when stimulated.

The percentage of dead adult arthropods was calculated for 1-, 4-, and 24-hour intervals following infestation and compared for efficacy to the data of the Control Groups. Table 15 summarizes the mean mortality data of the treatment against each arthropod at the stated intervals. The tested composition killed 100% of all arthropods by the 24-hour observation interval, and exhibited strong pesticidal activity against some species at the 4-hour observation interval.

TABLE 15

Mean % Mortality of 2-Hour Dried Compositions Against Arthropods.

| Insect | Treated/Control | Mean % Mortality | | | |
|---|---|---|---|---|---|
| | | 0 hrs | 1 hrs | 4 hrs | 24 hrs |
| Smoky Brown cockroach | Treated | 0 | 0 | 45 | 100 |
| Smoky Brown cockroach | Control | 0 | 0 | 0 | 0 |
| German cockroach | Treated | 0 | 0 | 93 | 100 |
| German cockroach | Control | 0 | 0 | 0 | 0 |
| American cockroach | Treated | 0 | 0 | 66 | 100 |
| American cockroach | Control | 0 | 0 | 0 | 0 |
| Cellar Spider | Treated | 0 | 11 | 33 | 100 |
| Cellar Spider | Control | 0 | 0 | 0 | 33 |
| Cat Flea | Treated | 0 | 100 | 100 | 100 |
| Cat Flea | Control | 0 | 0 | 0 | 0 |
| Tick | Treated | 0 | 7 | 100 | 100 |
| Tick | Control | 0 | 0 | 0 | 0 |
| Fire Ant | Treated | 0 | 100 | 100 | 100 |
| Fire Ant | Control | 0 | 0 | 10 | 100 |
| Termite | Treated | 0 | 100 | 100 | 100 |
| Termite | Control | 0 | 0 | 20 | 20 |
| Carpenter Ant | Treated | 0 | 10 | 80 | 100 |
| Carpenter Ant | Control | 0 | 0 | 0 | 0 |
| Pavement Ant | Treated | 0 | 100 | 100 | 100 |

TABLE 15-continued

Mean % Mortality of 2-Hour Dried Compositions Against Arthropods.

| Insect | Treated/Control | Mean % Mortality | | | |
|---|---|---|---|---|---|
| | | 0 hrs | 1 hrs | 4 hrs | 24 hrs |
| Pavement Ant | Control | 0 | 0 | 0 | 0 |
| Field Ant | Treated | 0 | 100 | 100 | 100 |
| Field Ant | Control | 0 | 0 | 0 | 0 |
| Moisture Ant | Treated | 0 | 100 | 100 | 100 |
| Moisture Ant | Control | 0 | 0 | 0 | 70 |
| Wood Ant | Treated | 0 | 100 | 100 | 100 |
| Wood Ant | Control | 0 | 0 | 0 | 0 |
| House Fly | Treated | 0 | 55 | 100 | 100 |
| House Fly | Control | 0 | 0 | 0 | 80 |
| Bottle Fly | Treated | 0 | 95 | 100 | 100 |
| Bottle Fly | Control | 0 | 0 | 0 | 0 |
| Giant Silverfish | Treated | 0 | 0 | 22 | 100 |
| Giant Silverfish | Control | 0 | 0 | 0 | 0 |
| Firebrat | Treated | 0 | 0 | 40 | 100 |
| Firebrat | Control | 0 | 0 | 0 | 0 |
| Bean aphid | Treated | 0 | 10 | 25 | 100 |
| Bean aphid | Control | 0 | 0 | 0 | 22 |
| Pea Aphid | Treated | 0 | 0 | 95 | 100 |
| Pea Aphid | Control | 0 | 0 | 0 | 33 |

Example 15—Broad Spectrum Pesticide Activity

This example illustrates the dry residue pesticidal activity of a combination of natural oil and solvent against arthropods (including insects, arachnids, millipedes and centipedes) other than bed bugs. The tested arthropods were granary weevil (*Sitophilus granarius*), maize weevil (*Sitophilus zeamais*), confused flour beetle (*Tribolium confusum*), rusty grain beetle (*Cryptolestes ferrugineus*), dust mite (*Dermatophagoides farinae*), millipede (*Cylindroiulus caeruleocinctus*), centipede (*Strigamia aluminata*), sowbug (*Oniscus asellus*), orabatid mite (*Haplozetes* sp.), house cricket (*Acheta domestica*), black widow spider (*Latrodectus mactans*), brown recluse spider (*Loxosceles reclusa*), pharaoh ant (*Monomorium pharaonis*).

A solution of 5.5% neem oil by weight, 18.25% acetophenone by weight and 1.25% ethoxylated castor oil by weight was combined with an appropriate amount of isopropyl alcohol as a carrier diluent ("treatment A"), or alternatively, a solution comprising 22% neem oil by weight, 73% acetophenone by weight and 5.0% ethoxylated castor oil by weight ("treatment B") was prepared. 0.64-1.2 mL of the solution was applied to filter paper surfaces, 90 millimeters in diameter, contained in petri dishes (the Treated Groups). Untreated Control replicates were tested concurrently.

Treated substrates were allowed to air dry for 2 hours (treatment A) or 4 hours (treatment B) prior to infestation with a known number of adult arthropods. Dishes were infested according to the following schedule: five replicates of five adults apiece were prepared for granary weevils, maize weevils, confused flour beetles and rusty grain beetles; three replicates of 10 adults apiece were prepared for millipedes; four replicates of 5 adults apiece were prepared for centipedes and pharaoh ants; 6 replicates of 5 adults apiece were prepared for sowbugs and dust mites; one replicate of 30 adults was prepared for orabatid mites; two replicates of 5 adults apiece were prepared for house crickets; and 20 replicates of 1 adult apiece were prepared for black widow spiders and brown recluse spiders. At 1-, 4-, and 24-hour intervals following the addition of arthropods, the number of arthropods killed in the intervening period was observed. The adult arthropods were counted dead if they were unresponsive when stimulated.

The percentage of dead adult arthropods was calculated for 1-, 4-, and 24-hour intervals following infestation and compared for efficacy to the data of the Control Groups. Table 16 summarizes the mean mortality data of the treatment against each arthropod at the stated intervals. The tested composition killed 100% of all arthropods by the 24-hour observation interval, and exhibited strong pesticidal activity against some species at the 1- and 4-hour observation interval.

TABLE 16

Mean % Mortality of 2- or 4-Hour Dried Compositions Against Arthropods

| Insect | Treated/ Control | Mean % Mortality | | | |
|---|---|---|---|---|---|
| | | 0 hrs | 1 hrs | 4 hrs | 24 hrs |
| Granary Weevil | Treated | 0 | 100 | 100 | 100 |
| Granary Weevil | Control | 0 | 0 | 0 | 0 |
| Maize Weevil | Treated | 0 | 100 | 100 | 100 |
| Maize Weevil | Control | 0 | 0 | 0 | 0 |
| Confused Flour Beetle | Treated | 0 | 0 | 0 | 100 |
| Confused Flour Beetle | Control | 0 | 0 | 0 | 0 |
| Rusty Grain Beetle | Treated | 0 | 100 | 100 | 100 |
| Rusty Grain Beetle | Control | 0 | 0 | 0 | 0 |
| Dust Mite | Treated | 0 | 100 | 100 | 100 |
| Dust Mite | Control | 0 | 0 | 3 | 7 |
| Millipede* | Treated | 0 | 0 | 83 | 100 |
| Millipede* | Control | 0 | 0 | 3 | 13 |
| Centipede* | Treated | 0 | 10 | 100 | 100 |
| Centipede* | Control | 0 | 0 | 0 | 5 |
| Sowbug* | Treated | 0 | 0 | 100 | 100 |
| Sowbug* | Control | 0 | 0 | 0 | 0 |
| Orabatid Mite* | Treated | 0 | 73 | 100 | 100 |
| Orabatid Mite* | Control | 0 | 0 | 0 | 0 |
| House Cricket* | Treated | 0 | 80 | 100 | 100 |
| House Cricket* | Control | 0 | 0 | 0 | 0 |
| Black Widow Spider* | Treated | 0 | 0 | 0 | 100 |
| Black Widow Spider* | Control | 0 | 0 | 0 | 0 |
| Brown Recluse Spider* | Treated | 0 | 0 | 0 | 80 |
| Brown Recluse Spider* | Control | 0 | 0 | 0 | 0 |
| Pharaoh Ant* | Treated | 0 | 0 | 95 | 100 |
| Pharaoh Ant* | Control | 0 | 0 | 0 | 0 |

(no asterisk = exposed to 2 h dry residual treatment A)
(* = exposed to 4 h dry residual treatment B)

Example 16—Dry Residual Pesticide Activity Against Insecticide-Resistant Insects This example illustrates the dry residue pesticidal activity of exemplary compositions against bed bugs resistant to pyrethroid insecticides, a recognized problem in eliminating bed bug infestations (see Romero). A formulation of 5.5% neem oil by weight, 15.5% acetophenone by weight, 8% natural oils (lemongrass oil, spearmint oil, clove oil, and wintergreen oil) by weight and 5.0% ethoxylated castor oil by weight was prepared and combined with an appropriate amount of isopropyl alcohol as a carrier diluent (the Treated Group). A concentrate formulation of the common pyrethroid insecticide Suspend® SC containing 4.75% deltamethrin by weight diluted according to the highest (strongest) rate allowed by the label was employed as a Positive Control Group. 1.0 mL of each solution was applied to filter paper surfaces, 90 millimeters in diameter, contained in petri dishes, and allowed to dry for two hours. Five replicates of each Treated Group, Positive Control Group, and a Negative Control Group were tested concurrently. Adult bed bugs from a field-collected strain were added to each treated surface. Mortality of bed bugs was observed at specified intervals after infestation on substrates. The adult bed bugs were counted dead if they were unresponsive when stimulated.

Figure 3:
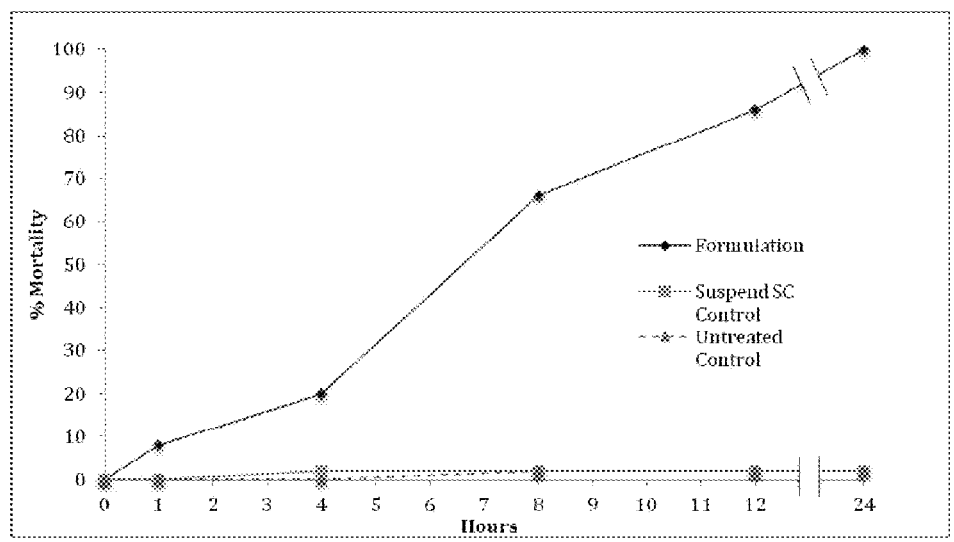
FIG. 3 shows the results of an example testing the ability of a composition in accordance with one embodiment of the invention to kill pyrethroid-resistant bed bugs.

The percentage of dead adult bed bugs at 0-, 1-, 4-, 8-, 12-, 24-, and 72-hour intervals on Treated Group were compared against those infested on the Positive Control (deltamethrin-treated) and Negative Control Groups. FIG. 3 summarizes the results as tested on filter paper. Bed bugs infested on deltamethrin (Positive Control Group) exhibited mean mortality of 10% by the 72-hour interval, which was statistically insignificant in comparison with Negative Controls. The tested formulation including neem oil and acetophenone produced 100% mortality by the 24-hour interval.

Example 17—Repellency of Exemplary Compositions

This example illustrates the repellency characteristics of an exemplary composition according to one embodiment. Where it is desired to have an insecticide act by killing or otherwise disrupting the life cycle of adult insects, nymphs, and their eggs, rather than merely dispersing them, repellent characteristics of the composition utilized may be reduced or minimized in some embodiments.

In this example, bed bug mortality was evaluated on a treated surface with an untreated crevice harbourage available, and the percentage of bed bugs that retreated to the untreated crevice was measured to evaluate the repellency of the tested compositions. Four solutions were prepared, each containing isopropanol as a carrier diluent: 'Solution A' included 5.5% neem oil by weight, 15.5% acetophenone by weight, 8% natural oils (lemongrass oil, spearmint oil, and wintergreen oil) by weight and 5.0% surfactant by weight; 'Solution B' included 5.5% neem oil by weight, 15.5% acetophenone by weight, and 5.0% surfactant by weight; 'Solution C' included 5.5% neem oil by weight, and 5.0% surfactant by weight; and 'Solution D' included 5.5% neem oil alone by weight. The surfactant used in all solutions was ethoxylated castor oil. Ninety-millimeter diameter filter paper substrates were prepared in petri dishes, on which were affixed small wooden blocks notched on one side, the notch forming a small crevice out of contact with the filter paper where insects could shelter. For the Treated Groups 1.0 mL of each solution was applied to the exterior of the block, leaving the crevice untreated, and 1.0 mL of each solution was applied directly to the filter paper substrate. A fifth untreated group was tested concurrently as a negative Control Group. Treated substrates were allowed to dry for two hours before infestation with adult bed bugs.

Immediately after treatment and at 1-, 4-, and 8-hour intervals after infestation of bed bugs to each group, the bed bugs were observed for mortality and whether they preferred to stay on the treated filter paper, or locate within the untreated crevice. Table 17 summarizes the observations of each Group immediately after infestation and at 1-, 4-, and 8-hour intervals post-infestation. Compositions A and B, which included neem oil in combination with acetophenone, exhibited a lesser degree of repellency (i.e. fewer bed bugs were counted in the untreated crevice) than compositions including neem oil alone, with or without surfactant (compositions C and D).

TABLE 17

Mean Repellency Data.

| Solution | 0-hour | | | | | 1-hour | | | 4-hour | | | | 8-hour | | |
|---|---|---|---|---|---|---|---|---|---|---|---|---|---|---|---|
| | % Live In Crev. | % Live Out Crev. | % Live In Crev. | % Live Out Crev. | % Dead | % Live In Crev. | % Live Out Crev. | % Dead | % Live In Crev. | % Live Out Crev. | % Dead |
| A | 0 | 100 | 0 | 100 | 0 | 0 | 22 | 78 | 0 | 0 | 100 |
| B | 0 | 100 | 10 | 90 | 0 | 0 | 0 | 100 | 0 | 0 | 100 |
| C | 0 | 100 | 40 | 60 | 0 | 70 | 30 | 0 | 20 | 10 | 70 |
| D | 0 | 100 | 100 | 0 | 0 | 80 | 20 | 0 | 60 | 0 | 40 |
| Control | 0 | 100 | 50 | 50 | 0 | 50 | 50 | 0 | 60 | 40 | 0 |

Example 18—Testing of Various Substrates

This example illustrates the pesticidal activity of a composition according to an exemplary embodiment on a variety of surfaces. In particular, the example demonstrates the dry residue pesticidal activity of an exemplary formulation on several substrates where bed bugs are known to live, nest, and reproduce indoors. A solution including 5.5% neem oil by weight, 15.5% acetophenone by weight, 8% natural oils (lemongrass oil, spearmint oil, clove oil, and wintergreen oil) by weight and 5.0% ethoxylated castor oil by weight was prepared and combined with an appropriate amount of isopropyl alcohol as a carrier diluent. Four substrates were prepared: painted plywood, 100% cotton fabric, mattress swatch, and Berber carpet (glued to the petri dish to prevent the test bugs from climbing underneath the carpet to escape the treated area). Five replicates were constructed for each Treated Group and five replicates were constructed for untreated Control Groups of each substrate. 1.0 mL of the formulation was applied to each Treated Group and allowed to dry for two hours. Adult bed bugs were infested two hours after treatment. Bed bugs were observed for mortality immediately after infestation and at 1-, 4-, 8-, 12-, 24-, and 72-hour intervals post-infestation. Bed bugs were counted dead if unresponsive when stimulated.

The percentage of dead adult bed bugs was calculated for each interval and compared to the data for all other groups. Table 18 presents the mean mortality data for the Treated and Control Groups over the stated intervals. Mortality of adult bed bugs for all Treated Groups was 100% at 24 hours and 100% for all treated surfaces excepting glued carpet (80% mortality) at 12 hours. This data indicates efficacy of the tested composition on a wide range of indoor surfaces.

TABLE 18

Mean % Bed Bug Mortality after Treatment on Various Substrates.

| | Time (Hours) | | | | | | |
|---|---|---|---|---|---|---|---|
| | 0 | 1 | 4 | 8 | 12 | 24 | 72 |
| Untreated Plywood | 0 | 2 | 6 | 4 | 4 | 6 | 6 |
| Treated Plywood | 0 | 2 | 58 | 98 | 100 | 100 | 100 |
| Untreated Cotton | 0 | 0 | 2 | 2 | 6 | 8 | 16 |
| Treated Cotton | 0 | 28 | 82 | 100 | 100 | 100 | 100 |
| Untreated Mattress | 0 | 2 | 2 | 4 | 4 | 4 | 12 |
| Treated Mattress | 0 | 42 | 98 | 100 | 100 | 100 | 100 |
| Untreated Glued Carpet | 0 | 0 | 0 | 0 | 0 | 0 | 0 |
| Treated Glued Carpet | 0 | 0 | 0 | 30 | 80 | 100 | 100 |

Example 19—Residual Activity of Various Solvent/Oil Combinations

This example illustrates the dry residual pesticidal activity of formulations comprising varying pesticidal natural oils (oregano, clove and cinnamon oils) with acetophenone as the polar aromatic solvent. Solutions were prepared using 5.5% by weight natural oil; the percent by weight of acetophenone indicated in Table 19 and an appropriate amount of isopropanol as a carrier diluent. The percent by weight of solvent was at a final concentration of 1.5 mol/kg. Solutions were also prepared of each natural oil alone (5.5% by weight with an appropriate amount of isopropanol as a carrier diluent), and of acetophenone alone (the percent by weight indicated in Table 19 with an appropriate amount of isopropanol as a carrier diluent). Treated Groups for each solution were prepared by treating filter paper, 90 mm in diameter, with 1.0 mL of solution and allowing it to air dry for four hours. A known number of adults (usually 10) were added to each treated dish, four hours after treatment. Bed bug mortality was assessed immediately after infestation and at 1-hour, 2-hour, 4-hour, 6-hour, 8-hour, 10 hour, 12-hour, and 24-hour intervals, and at 24-hour intervals thereafter until 14 days after infestation. Adult bed bugs were counted dead if they were unresponsive when stimulated. Table 19 shows the maximum % mortality of all treated groups and the time taken to reach maximum mortality. Combinations of a pesticidal oil and acetophenone were more effective than either the oil or acetophenone alone.

TABLE 19

Maximum % Mortality of Various Oils Alone or With Acetophenone

| Oil | Solvent | Solvent % w/w | Max Mortality | Time | LT50 |
|---|---|---|---|---|---|
| Oil Controls | | | | | |
| Oregano oil | — | — | 100% | 72 h | 18 h |
| Clove oil | — | — | 100% | 53 h | 17 h |
| Cinnamon oil | — | — | 90% | 218 h | 22 h |
| Oil + Acetophenone | | | | | |
| Oregano oil | Acetophenone | 18.25 | 100% | 24 h | 6 h |
| Clove oil | Acetophenone | 18.25 | 100% | 24 h | 8 h |
| Cinnamon oil | Acetophenone | 18.25 | 100% | 53 h | 8 h |
| — | Acetophenone | 18.25 | 100% | 53 h | 17 h |

Example 20—Residual Activity of Various Oils in Combination with Acetophenone

This example illustrates the dry residual pesticidal activity of formulations comprising further pesticidal natural oils (thyme, garlic and neem oils) with acetophenone as the polar aromatic solvent. Solutions were prepared using 5.5% by weight natural oil; the percentage by weight of organic solvent indicated in Table 20 and an appropriate amount of isopropanol as a carrier diluent. Solvent was added to a final concentration of 1.5 mol/kg. Solutions were also prepared of each natural oil alone (5.5% by weight with an appropriate amount of isopropanol as a carrier diluent), and of the polar organic solvent alone (the percent by weight indicated in Table 20 with an appropriate amount of isopropanol as a carrier diluent). Treated Groups for each solution were prepared by treating filter paper, 90 mm in diameter, with 1.0 mL of solution and allowing it to air dry for four hours. A known number of adults (usually 10) were added to each treated dish, four hours after treatment. Bed bug mortality was assessed immediately after infestation and at 1-hour, 2-hour, 4-hour, 6-hour, 8-hour, 10 hour, 12-hour, and 24-hour intervals, and at 24-hour intervals thereafter until 14 days after infestation. Adult bed bugs were counted dead if they were unresponsive when stimulated. Table 20 shows the maximum % mortality of all treated groups and the time taken to reach maximum mortality. Combinations of a pesticidal oil and acetophenone were more effective than either the oil or acetophenone alone.

TABLE 20

Maximum % Mortality of Various Oils Alone or With Acetophenone

| Oil | Solvent | Solvent % w/w | Max Mortality | Time | LT50 |
|---|---|---|---|---|---|
| Oil Controls | | | | | |
| Oregano oil | — | — | 100% | 24 h | 8 h |
| Clove oil | — | — | 100% | 150 h | 27 h |
| Cinnamon oil | — | — | 100% | 150 h | 37 h |
| Thyme | — | — | 100% | 150 h | 36 h |
| Garlic | — | — | 100% | 150 h | 22 h |
| Neem oil | — | — | 10% | — | — |
| Oil + Acetophenone | | | | | |
| Thyme | Acetophenone | 18.25 | 100% | 10 h | 6 h |
| Garlic | Acetophenone | 18.25 | 100% | 10 h | 7 h |
| Neem oil | Acetophenone | 18.25 | 100% | 8 h | 4 h |
| — | Acetophenone | 18.25 | 100% | 48 h | 11 h |

Various references are mentioned or pertinent to the discussion herein, including for example the References listed below. The disclosures of each of the following references are incorporated by reference in their entireties.

REFERENCES

JP Appl. No. 50042053
U.S. Appl. No. 12,112,632 Bessette et al.
U.S. Appl. No. 12,598,353 Bessette et al.
U.S. Pat. No. 2,793,154 Shillitoe et al.
U.S. Pat. No. 2,897,112 Manufacturers Association Inc.
U.S. Pat. No. 4,283,878 Hill et al.
U.S. Pat. No. 4,556,562 Larson et al.
U.S. Pat. No. 5,145,604 Neumiller et al.
U.S. Pat. No. 5,405,612 Locke et al.
U.S. Pat. No. 5,472,700 Steatz et al.
U.S. Pat. No. 5,679,662 Chang et al.
U.S. Pat. No. 5,792,465 Hagarty et al.
U.S. Pat. No. 5,885,600 Blum et al.
U.S. Pat. No. 6,294,571 Subbaraman et al.
U.S. Pat. No. 6,703,034 Parmar et al.
U.S. Pat. No. 7,381,431 Baker et al.
U.S. Pat. No. 7,687,533 Critcher et al.
Abbassy, M. A., et al., "Insecticidal and synergistic effects of *Majorana hortensis* essential oil and some of its major constituents" (2009) 131:3 Entomologia Experimentalis et Applicata 225-232.
Ahmed, K S, et al, "Effects of plant oils on oviposition preference and larval survivorship of *Callosobruchus chinensis* on azuki bean" (1999) 34:4 Applied Entomology and Zoology 547-550.
Ansaria, M A, et al., "Larvicidal and mosquito repellent action of peppermint (*Mentha piperita*) oil" (2000) 71:3 Bioresource Technology 267-271.
Arslan, N, et al., "Variation in Essential Oil Content and Composition in Turkish Anise (*Pimpinella anisum* L.) Populations" (2004) 28 Turk. J. Agri. For. 173-177.
Avato, P., et al., "Allylsulfide constituents of garlic volatile oil as antimicrobial agents" (2000) 7:3 Phytomedicine 239-243.
Barnard, D. R., "Repellency of Essential Oils to Mosquitoes (*Dipthera culicidae*)" (1999) 36:5 Journal of Medical Entomology 625-629.
Brachmachari, G, "Neem—an omnipotent plant: a retrospection" (2004) 5 Chembiochem 408-421.
Chaieb, K, et al., "The chemical composition and biological activity of clove essential oil, *Eugenia caryophyllata* (*Syzigium aromaticum* L. Myrtaceae): a short review" (2007) 21:6 Phytotherapy Research 501-506.
Chang, K. S. and Ahn, Y. T., "Fumigant activity of (E)-anethole identified in *Illicium verum* fruit against *Blattella germanica*" (2001) 58 Pest Manage. Sci. 161-166.
Chang, S. T. and Cheng, S. S., "Antitermitic activity of leaf essential oils and components from *Cinnamomum osmophleum*" (2002) 50 J. Agric. Food Chem. 1389-1392.
Cheng, S. S., et al., "Variations in insecticidal activity and chemical compositions of leaf essential oils from *Cryptomeria japonica* at different ages" (2009) 100:1 Bioresource Tech. 465-470.
Choi, W, et al, "Toxicity of Plant Essential Oils to *Tetranychus urticae* (Acari: Tetranychidae) and *Phytoseiulus persimilis* (Acari: Phytoseiidae)" (2004) 97:2 Journal of Economic Entomology, 553-558.
Clark, R. J. & Menary, R. C., "Variations in Compositions of Peppermint Oil in Relation to Production Areas" (1981) 35 Econ. Bot. 59-69.

Daniel, S H & Smith, R H, "The repellent effect of neem (*Azadirachta indica* A Juss) oil and its residual efficacy against *Callosobruchus maculatus* on cowpea" in Fleurat-Lessard, F, & Ducom, P, eds, *Proceedings Fifth International Working Conference on Stored-Product Protection* (Bordeaux, 1990) 1589.

Don-Pedro, K. M. "Investigation of single and joint fumigant insecticidal action of citrus peel oil components" (1996) 46 Pestic. Sci. 79-84.

Ellis, M. D. and Baxendale, F. P., "Toxicity of seven monoterpenoids to tracheal mites (Acari: Tarsonemidae) and their honey bee (Hymenoptera: Apidae) hosts when applied as fumigants" (1997) 90 J. Econ. Entomol. 1087-1091.

Erbilgin et al., "Acetophenone as an anti-attractant for the Western Pine Beetle, *Dendroctonus brevicomis* LeConte" (2007) 33 J Chem. Ecol. 817-823.

Franzios, G., et al. "Insecticidal and genotoxic activities of mint essential oils (1997) 45 J. Agric. Food Chem. 2690-2694.

Fuhremann, T. W., et al., "Effects of naturally occurring food plant components on insecticide degradation in rats" (1978) 26:5 J. Agri. Food Chem. 1068-1075.

Gahukar, R T, "Formulations of neem based products/pesticides" (1996) 20(9) Pestology 44-45.

Gochev, V., et al., "Chemical Composition and Antimicrobial Activity of Bulgarian Peppermint Oils" (2008) 36:5 Bulgaria Scientific Papers 83.

Granger & Passet, "*Thymus vulgaris* spontane de France: Races chimiques et chemotaxonomie" (1973) 12:7 Phytochemistry 1683.

Harwood, S. H., Modenke, A. F. and Berry, R. E., "Toxicity of peppermint monoterpenes to the variegated cutworm (Lepidoptera: Noctuidae)" (1990) 83 J. Econ. Entomol. 1761-1767.

Hierro, I., Valero, A., Perez, P., Gonzalez, P., Cabo, M. M. and Navarro, M. C., "Action of different monoterpenic compounds against *Anisakis simplex* S.1.L. larvae" (2004) 11 Phytomedicine 77-82.

Hui, L, et al., "Chemical composition of lavender essential oil and its antioxidant activity and inhibition against rhinitis-related bacteria" (2010) 4:4 Afri. J. of Micro. Res. 309-313.

Hummelbrunner, A. L. and Isman, M. B., "Acute, sublethal, antifeedant and synergistic effects of monoterpenoid essential oil compounds on the tobacco cut worm (Lepidoptera: Noctuidae)" (2001) 49 J. Agric. Food Chem. 715-720.

Jones, C. & Firn, R., "Some Allelochemicals of *Ptteridium quilinum* and their Involvement in Resistance to *Pieris brassicae*" (1979) 7 Biochem. Syst. Ecol. 187.

Karr, L. L. and Coats, J. R. "Effects of four monoterpenoids on growth and reproduction of the German cockroach (Blattodea: Blattellidae)" (1992) 85 J. Econ. Entomol. 424-429.

Kaul, P. N., et al., "Volatile constituents of essential oils isolated from different parts of cinnamon (*Cinnamomum zeylanicum* Blume), (2003) 83 J. Sci. Food Agri. 53-55.

Khattak, M K, "Repellancy and residual effect of neem or mineral oil on the distribution and oviposition of maize weevil, *Sitophilus zeamus* Motsch" (2000) 3 Pakistan Journal of Biological Sciences 2131-2134.

Kim E H, Kim H K, Ahn Y J, "Acaricidal activity of clove bud oil compounds against *Dermatophagoides farinae* and *Dermatophagoides pteronyssinus* (Acari: Pyroglyphidae)" (2003) 51 J Agric Food Chem 885-889.

Kimbaris, A. C., et al., "Quantitative analysis of garlic (*Allium sativum*) oil unsaturated acyclic components using FT-Raman spectroscopy" (2006) 94:2 Food Chemistry 287-295.

Lee, S., Tsao, R., Peterson, C. and Coats, J. R., "Insecticidal activity of monoterpenoids to western corn root worm (Coleoptera: *Chrysomelidae*), spotted spidermite (Acari: Tetranychidae) and Housefly (Diptera: Muscidae)" (1997) 90 J. Econ. Entomol., 883-892.

Lota, M.-L., et al., "Volatile Components of Peel and Leaf Oils of Lemon and Lime Species" (2002) 50 J. Agri. Food Chem. 796-805.

Marcus, C. & Lichtenstein, P., "Biologically Active Components of Anise: Toxicity and Interactions with Insecticides in Insects" (1979) 27:6 J. Agri. Food Chem. 1217.

Miresmailli, S., Bradbury, R. and Isman, M. B., "Comparative toxicity of *Rosmarinus officinalis* L. essential oil blends of its major constituents against *Tetranychus urticae* Koch (Acari: Tetranychidae) on two different host plants" (2006) 62 Pest Manag. Sci. 366-371.

Mishra, A K, et al, "Use of neem oil as a mosquito repellent in tribal villages of mandla district, madhya pradesh" (1995) 32:3 Indian J Malariol 99-103.

Momen, F M, et al, "Influence of Mint and Peppermint on *Tetranychus urticae* and Some Predacious Mites of the Family Phytoseiidae (Acari: Tetranychidae: Phytoseiidae)" (2001) 36 Acta Phytopathologica et Entomologica Hungarica 143-153.

Naovi, S N H, et al., "Comparative Toxicity of RB-A [Neem Formulation] and Malathion Against Bed Bugs" (1993) 13 *Proceedings of Pakistan Congress of Zoology* 369.

National Research Council, Board on Science and Technology for International Development, Ad Hoc Panel Report, *Neem: A Tree for Solving Global Problems* (Washington: National Academy Press, 1992).

Obeng-Ofori, D. and Reichmuth, C. H., "Bioactivity of eugenol, a major component of essential oil of *Ocimum suvae* (wild) against four species of stored product coleopteran" (1997) 43 Int. J. Pest Manag. 89-94.

Pavela, R., Kazda, J., & Herda, G., "Effectiveness of Neem (*azidirachta indica*) insecticides against *Brassica* pod midge (*Dasinera brassicae* Winn.)" (2009) 82:3 Journal of Pest Science 235.

Perrucci, S., Cioni, P. L., Cascella, A., Macchioni, F., "Therapeutic efficacy of linalool for the topic treatment of parasitic otitis caused by *Psoroptes cuniculi* in the rabbit and in the goat" (1997) 11 Med. Vet. Entomol. 300-302.

Rahman, A & Talukder, F A, "Bioefficacy of somer plant derivatives that protect grain against the pulse beetle, *Callosobruchus maculatus*" (2006) 6:3 Journal of Insect Science.

Rajeswara Rao, B. R., et al., "Volatile flower oils of three genotypes of rose-scented geranium (*Pelargonium* sp.)" (1999) 15 Flavour Frag. J. 105-107.

Romero, A, et al, "Insecticide Resistance in the Bed Bug: A Factor in the Pest's Sudden Resurgence" (2007) 44:2 J Med Entomol 175.

Salom, S. M., et al., "Laboratory Evaluation of Biologically-Based Compounds as Antifeedants for the Pales Weevil, Hulobius-Pales (Herbst)" (1994) 29 J. Entomol. Sci. 407.

Samarasekera, R, "Mosquitocidal Activity of Leaf and Bark Essential Oils of Ceylon *Cinnamomum zeylanicum*" (2005) 17:3 Journal of Essential Oil Research 301-303.

Santos, P. M., et al., "Essential oils from hairy root cultures and from fruits and roots of *Pimpinella anisum*" (1998) 48 Phytochemistry 455-460.

Schumutter, H, "Properties and potential of natural pesticides from the neem tree, *Azadirachta indica*" (1990) 35 Annu Rev Entomol 271.

Shabnum S., Wagay M., "Essential Oil Composition of *Thymus Vulgaris* L. and their Uses" (2011) Journal of Research & Development, Vol. 11

Shellie R, Mondello L, Marriott P, Dugo G., "Characterisation of lavender essential oils by using gas chromatography-mass spectrometry with correlation of linear retention indices and comparison with comprehensive two-dimensional gas chromatography" (2002) 970 J. Chromatogr. A. 225-234.

Simic, A., et al., "The Chemical Composition of some Lauraceae Essential Oils and Their Antifungal Activities" (2004) 18 Phytother. Res. 713-717.

Thompson, J. et al., "Qualitative and quantitative variation in monoterpene co-occurrence and composition in the essential oil of *Thymus vulgaris* chemotypes" (2003) 29 J. Chem. Ecol. 859.

Toncer, O., et al., "Changes in Essential Oil Composition of Oregano (*Origanum onites* L.) due to Diurnal Variations at Different Development Stages" (2009) Notulae Botanicae Horti Agrobotanici Cluj 37 (2), 177-181.

Traboulsi, A. F., et al., "Insecticidal properties of essential plant oils against the mosquito *Culex pipiens molestus* (Diptera: Culicidae)" (2002) 58:5 Pest Manag. Sci. 491-495.

Tripathi, A. K., et al., Effects of volatile oil constituents of *Mentha* species against stored grain pests, *Callosobrunchus maculatus* and *Tribolium castanum*" (2000) 22 J. Med. Arom. Plant Sci. 549-556.

Tripathi, A. K., Prajanpati, V., Aggarwal, K. K. and Kumar, S., "Toxicity, feeding deterrence, and effect of activity of 1,8-cineole from *Artemisia annua* on progeny production of *Tribolium castanaeum* (Coleoptera: Tenebrionidae)" (2001) 94 J. Econ. Entomol. 979-983.

Trongtokit Y, Rongsriyam Y, Komalamisra N, Apiwathnasorn C., "Comparative repellency of 38 essential oils against mosquito bites" (2005) 19 Phytother Res 303-309.

Vasudeva, N. & Sharma, T., "Chemical Composition and Antimicrobial Activity of Essential Oil of Citrus limettoides Tanaka" (2012) 1 Jour. Of Pharm. Tech. & Drug Res.

Vokou, D, et al., "Geographic variation of Greek Oregano (*Origanum vulgare* ssp. *hirtum*) essential oils" (1993) 21 Biochem. Syst. Ecol. 287-295.

Webb et al., On *the penetration of insecticides through the insect cuticle* (Cooper Technical Bureau: Berkhamsted, 1945).

Xia, Y, et al, "The molecular and cellular basis of olfactory-driven behaviour in *Anopheles gambiae* larvae" (2008) 105 Proceedings from the National Academy of Sciences 6433-6438.

Yang Y C, Lee S H, Lee W J, Choi D H, Ahn Y J, "Ovicidal and adulticidal effects of *Eugenia caryophyllata* bud and leaf oil compounds on *Pediculus capitis*" (2003) 51 J. Agri. Food Chem. 4884-4888.

Yang, Y. C., Lee, H. S., Lee, S. H., Clark, J. M., Ahn, Y. J., "Ovicidal and adulticidal activities of *Cinnamomum zeylanicum* bark essential oil compounds and related compounds against *Pediculus humanus capitis* (Anoplura: Pediculidae)" (2005) Int. J. Parasitol The invention described herein is not to be limited in scope by the specific aspects herein disclosed, since these aspects are intended as illustrations of several aspects of the invention. Any equivalent aspects are intended to be within the scope of this invention. Various modifications of embodiments of the invention in addition to those shown and described herein will become apparent to those skilled in the art from the foregoing description. Such modifications are also intended to fall within the scope of the appended claims and any claims hereafter introduced. To the extent that they are not mutually exclusive, embodiments described above can be combined with one another to yield further embodiments of the invention.

What is claimed is:

1. A method of killing pests comprising exposing the pests or their eggs to a composition comprising between 0.25% and 75% w/w of a pesticidal natural oil and between 0.7% and 75% w/w of a polar aromatic solvent, wherein:
    the polar aromatic solvent is an aryl ketone; and
    the pesticidal natural oil is one or more of neem oil, oregano oil, clove oil, cinnamon oil, thyme oil, garlic oil, lavender oil, peppermint oil, lime oil, geranium oil, anise oil, or eugenol.

2. The method as defined in claim 1, wherein the pests are arthropods.

3. The method as defined in claim 2, wherein the arthropods are insects, arachnids, centipedes or millipedes.

4. The method as defined in claim 3, wherein the insects are of the orders Hemiptera, Hymenoptera, Blattodea, Isoptera, Diptera, Lepidoptera, Thysanoptera, Thysanura, Coleopteran, Siphonaptera, Phthiraptera, Psocidae, Dermaptera, or Orthoptera.

5. The method as defined in claim 2, wherein the arthropods are bed bugs, cockroaches, flies, ants, ticks, fleas, sowbugs, pillbugs, centipedes, millipedes, spiders, silverfish, scorpions, aphids, scabies, lice, stink bugs, moths, beetles, lace bugs, aphids, thrips, moths, leafminers, grasshoppers, crickets, locusts, leafhoppers, planthoppers, psyllids, scale insects, midges, worms, milkweed bugs, mealy bugs, weevils, rice bugs, coffee bugs, vegetable bugs, corn borers, or mites.

6. The method as defined in claim 2, wherein the arthropods are bed bugs (*Cimex lectularius*), German cockroaches (*Blattella germanica*), Smoky Brown cockroaches (*Periplaneta fuliginosa*), American cockroaches (*Periplaneta americana*), cat fleas (*Ctenocephalides felis*), fire ants (*Solenopsis Invicta*), black carpenter ants (*Camponotus pennsylvanicus*), pavement ants (*Tetramorium caespitum*), field ants (*Formica* sp.), moisture ants (*Lasius* sp.), wood ants (*Formica rufa*), house flies (*Musca domestica*), bottle flies (*Lucilia sericata*), giant silverfish (*Ctenolepisma longicaudata*), firebrats (*Thermobia domestica*), bean aphids (*Aphis fabae*), pea aphids (*Acyrthosiphon pisum*), termites (*Reticulitermes flavipes*), granary weevils (*Sitophilus granarius*), maize weevils (*Sitophilus zeamais*), confused flour beetles (*Tribolium confusum*), rusty grain beetles (*Cryptolestes ferrugineus*), dust mites (*Dermatophagoides farinae*), millipedes (*Cylindroiulus caeruleocinctus*), centipedes (*Strigamia aluminata*), sowbugs (*Oniscus asellus*), orabatid mites (*Haplozetes* sp.), house crickets (*Acheta domestica*), black widow spiders (*Latrodectus mactans*), brown recluse spiders (*Loxosceles reclusa*), or pharaoh ants (*Monomorium pharaonis*).

7. The method as defined in claim 1, wherein the pesticidal natural oil is neem oil and the polar aromatic solvent is acetophenone.

8. The method as defined in claim 1, wherein the polar aromatic solvent is selected from the group consisting of: aryl-alkyl ketones and aryl-aryl ketones.

9. The method as defined in claim 1, wherein the polar aromatic solvent is acetophenone, 4'-methylacetophenone, 2',4'-dimethylacetophenone, 3',4'-dimethylacetophenone, propiophenone, 4'-methylpropiophenone, butyrophenone, isobutyrophenone, valerophenone, 4' hydroxyvalerophenone, hexanophenone, 2,2'-4,4' tetrahydroxybenzophenone, cyclohexyl phenyl ketone, 4'-hydroxyacetophenone, or 2'-hydroxyacetophenone.

10. The method as defined in claim 1, wherein the composition is provided as a liquid, emulsion, solid, wax, dust, fumigant, aqueous suspension, oily dispersion, paste, powder, emulsifiable concentrate, aerosol spray, wood filler, varnish, wood treatment, furniture oil, detergent, drywall mixture, fumigating candle, caulking composition, crack and crevice filler, sealing agent, or mattress and mattress cover treatment.

11. The method as defined in claim 1, wherein the pests are located indoors, in or at households, in or at commercial buildings or spaces, in shipping containers, in greenhouses, outdoors, or on agricultural land.

12. The method as defined in claim 1, wherein the method comprises preventing eclosion of pest eggs by killing the eggs by applying the composition to the eggs or to a surface where pests may deposit their eggs.

13. The method as defined in claim 12, wherein the pests are arthropods.

14. The method as defined in claim 13, wherein the arthropods are of the orders Blattellidae, Orthoptera, or Hemiptera.

15. The method as defined in claim 13, wherein the arthropods are bed bugs or cockroaches.

16. The method as defined in claim 1 comprising applying the composition directly to the pests or to surfaces where the pests or their eggs may contact or otherwise be exposed to the composition, waiting at least 7 days, 8 days, 9 days, 10 days, 11 days, 12 days, 13 days, 14 days, 15 days, 16 days, 17 days, 18 days, 19 days, 20 days, or 21 days, and then re-applying the composition directly to the pests, or to surfaces where the pests or their eggs may contact or otherwise be exposed to the composition.

17. The method as defined in claim 1, wherein the method comprises applying the composition in either liquid or vapor form.

18. The method as defined in claim 1, wherein the method comprises applying the composition to surfaces inside or at a household, residence, structure, building or other enclosed space.

19. The method as defined in claim 1, wherein the method comprises applying the composition to mattresses, sheets, fabrics, carpets, painted or unpainted hard surfaces, wood, flooring, furniture, travel bags or suitcases.

20. The method as defined in claim 1, wherein the method comprises combining the composition with natural oils for direct application, diluting the composition with an appropriate carrier for delivery as a ready-to-use spray, or providing the composition in a concentrated form to be diluted and applied by an end user.

21. The method as defined in claim 1, wherein the method comprises applying the composition as a wood treatment, as a furniture oil, as a laundry detergent, as a gel or paste applied to a target location, as an oily emulsion, as a dust formulation, as a component in drywall mixture, as a crack or crevice filler or other sealing agent, as a component in caulking compositions, as a fumigating mist or candle, or as a formulation employed for treating mattresses or mattress covers.

22. The method as defined in claim 1, comprising applying the composition to plants, parts of plants, or the soil surrounding plants.

\* \* \* \* \*